United States Patent
Barak

[11] Patent Number: 6,048,358
[45] Date of Patent: *Apr. 11, 2000

[54] METHOD AND APPARATUS FOR HEMOSTASIS FOLLOWING ARTERIAL CATHETERIZATION

[76] Inventor: Shlomo Barak, 27 Smilansky Street, Rishon le Zion, Israel

[*] Notice: This patent is subject to a terminal disclaimer.

[21] Appl. No.: 09/114,817

[22] Filed: Jul. 13, 1998

[51] Int. Cl.⁷ .................................................. A61B 17/08
[52] U.S. Cl. .......................................... 606/213; 606/215
[58] Field of Search ................................... 606/214, 213, 606/215; 604/93, 96, 118

[56] References Cited

U.S. PATENT DOCUMENTS

| | | | |
|---|---|---|---|
| 5,370,660 | 12/1994 | Weinstein et al. | 606/215 |
| 5,486,195 | 1/1994 | Myers et al. | 606/213 |
| 5,645,566 | 7/1997 | Brenneman et al. | 606/213 |
| 5,700,277 | 12/1997 | Nash et al. | 606/213 |
| 5,725,551 | 3/1998 | Myers et al. | 606/213 |
| 5,728,134 | 3/1998 | Barak | 606/214 |
| 5,853,421 | 12/1998 | Leschinsky et al. | 606/213 |
| 5,928,266 | 7/1999 | Kontus | 606/213 |

FOREIGN PATENT DOCUMENTS

WO 98/11830  3/1998  WIPO .

*Primary Examiner*—Gary Jackson
*Attorney, Agent, or Firm*—Townsend and Townsend and Crew LLP

[57] ABSTRACT

Apparatus and a method for hemostasis of an artery having a puncture after arterial catheterization, the apparatus comprising a catheter introducer having a forward and and a balloon adjacent said forward end, wherein the catheter introducer is constructed such that inflation of the balloon adjacent the forward end of the catheter introducer in engagement with an outer wall surface of the artery causes the forward end of the catheter introducer to be withdrawn completely from the wall of the artery and spaced therefrom.

33 Claims, 22 Drawing Sheets

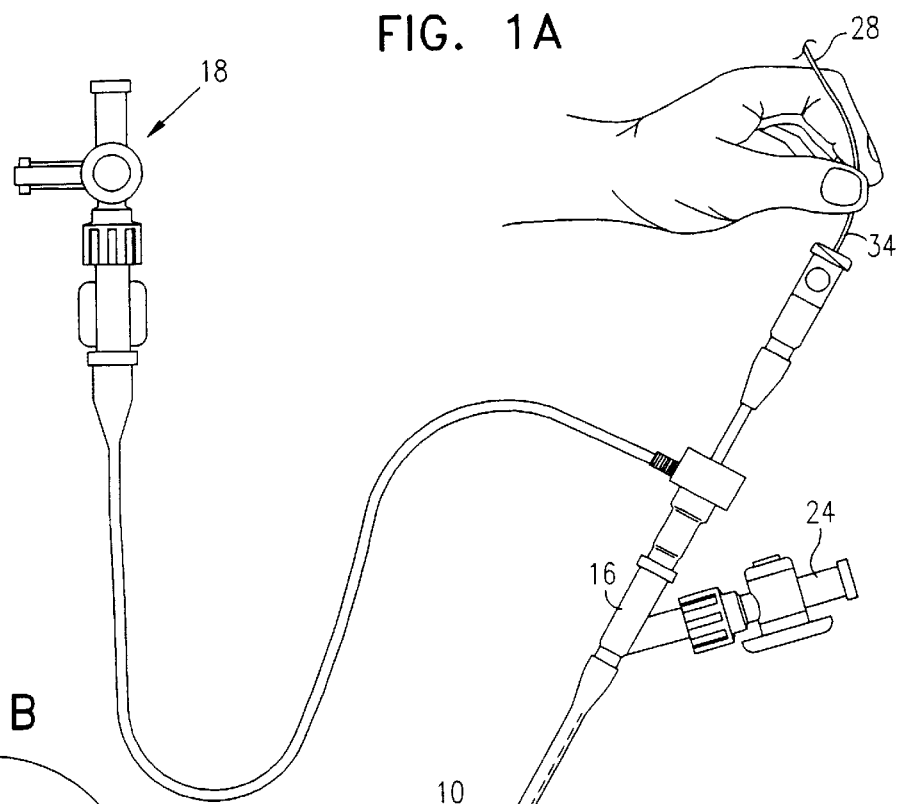
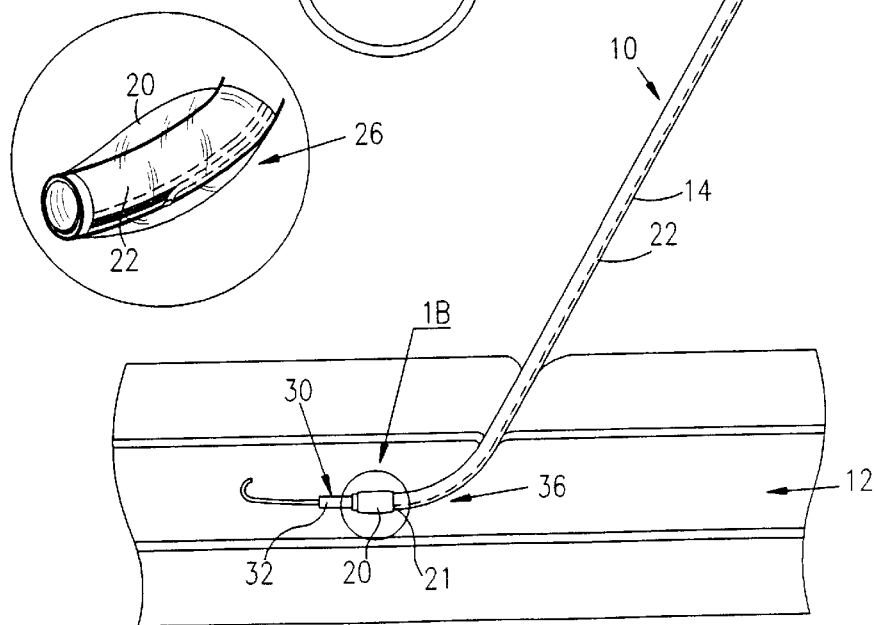

METHOD AND APPARATUS FOR HEMOSTASIS FOLLOWING ARTERIAL CATHETERIZATION

FIELD OF THE INVENTION

The present invention relates to methods and apparatus for hemostasis following arterial catheterization.

BACKGROUND OF THE INVENTION

Various techniques are known for arterial catheterization. Following arterial catheterization, it is necessary to cause hemostasis quickly and without undue hardship for the patient.

Applicant's U.S. Pat. No. 5,728,134 and Published PCT Patent application WO 98/11830 describe a method and apparatus for hemostasis which greatly simplifies hemostasis and thus greatly reduces patient discomfort following arterial catheterization. The prior art referenced in Applicant's Published PCT Patent application WO 98/11830 and U.S. Pat. No. 5,728,134 is considered to represent the state of the art.

SUMMARY OF THE INVENTION

The present invention seeks to provide improved apparatus and techniques for hemostasis.

There is thus provided in accordance with a preferred embodiment of the present invention a method for hemostasis of an artery having a puncture after arterial catheterization, the catheterization using an introducer sheath, the method including the steps of:

inserting into an artery a catheter introducer having a forward end and a balloon adjacent the forward end prior to arterial catheterization;

following arterial catheterization and removal of a catheter from the catheter introducer, introducing an inflatable anchor into the artery via the catheter introducer;

inflating the inflatable anchor inside the artery;

retraction of the anchor, until it engages the forward end of the catheter introducer and further engages an inner wall surface of a wall of the artery, whereby the catheter introducer is also retracted such that the forward end thereof lies in the vicinity of the wall of the artery, whereby the anchor blocks blood flow from the artery at the catheter introducer and the balloon adjacent the forward end of the catheter introducer lies outside an outer surface of the wall of the artery;

inflating the balloon adjacent the forward end of the catheter introducer sufficiently to cause the forward end of the catheter introducer to be withdrawn completely from the wall of the artery and simultaneously to prevent blood flow from the artery through the artery wall;

deflating the inflatable anchor and withdrawal thereof from the artery; and following hemostasis, deflating of the balloon adjacent the forward end of the catheter introducer and removal of the catheter introducer from the patient.

Preferably, the method also includes the step of injecting a hemostatic agent via the catheter introducer to a location external of the artery.

There is also provided in accordance with a preferred embodiment of the present invention apparatus for hemostasis of an artery having a puncture after arterial catheterization, the apparatus including a catheter introducer having a forward end and a balloon adjacent the forward end, wherein the catheter introducer is constructed such that inflation of the balloon adjacent the forward end of the catheter introducer in engagement with an outer wall surface of the artery causes the forward end of the catheter introducer to be withdrawn completely from the wall of the artery and spaced therefrom.

Preferably, the apparatus also includes an inflatable anchor suitable for introduction into an artery via the catheter introducer.

In accordance with a preferred embodiment of the present invention, the apparatus also includes a selectable inflator for inflating the inflatable anchor inside the artery.

Additionally in accordance with a preferred embodiment of the present invention, the apparatus additionally includes an injector for injecting a hemostatic agent via the catheter introducer to a location external of the artery.

In accordance with a preferred embodiment of the present invention, the forward edge of the catheter introducer extends forwardly less than the extent of the balloon when inflated. Preferably, the forward edge of the catheter introducer extends less than 4 mm beyond the forward edge of the balloon when not inflated.

There is additionally provided in accordance with a preferred embodiment of the present invention a method for hemostasis of an artery having a puncture after arterial catheterization, the catheterization using an introducer sheath, the method including the steps of:

inserting into an artery a catheter introducer having a forward end prior to arterial catheterization;

following arterial catheterization, introducing a hemostasis catheter into the artery via the catheter introducer, the hemostasis catheter including an inflatable anchor at a forward end thereof and a balloon adjacent the forward end thereof and spaced from the inflatable anchor;

inflating the inflatable anchor inside the artery;

retraction of the hemostasis catheter, until the inflatable anchor engages the forward end of the catheter introducer and further engages an inner wall surface of a wall of the artery, whereby the anchor blocks blood flow from the artery and the balloon adjacent the forward end of the hemostasis catheter lies outside an outer surface of the wall of the artery;

removing the catheter introducer at least from the vicinity of the artery;

partially inflating the balloon adjacent the forward end of the hemostasis catheter sufficiently to prevent blood flow from the artery through the artery wall;

deflating of the inflatable anchor;

further inflating the balloon adjacent the forward end of the hemostasis catheter, sufficiently to cause the forward end of the hemostasis catheter to be withdrawn completely from the wall of the artery; and following hemostasis, deflating the balloon adjacent the forward end of the hemostasis catheter and removal of the hemostasis catheter from the patient.

Preferably, the method also includes the step of injecting a hemostatic agent via the catheter introducer to a location external of the artery.

Additionally in accordance with a preferred embodiment of the present invention there is provided apparatus for hemostasis of an artery having a puncture after arterial catheterization, the apparatus including:

an hemostasis catheter including an inflatable anchor at a forward end thereof and a balloon adjacent the forward end thereof and spaced from the inflatable anchor; and a selectable inflator for inflating the inflatable anchor inside the artery;

wherein the hemostasis catheter is constructed such that inflation of the balloon adjacent the forward end of the hemostasis catheter in engagement with an outer wall surface of the artery causes the forward end of the hemostasis catheter to be withdrawn completely from the wall of the artery and spaced therefrom.

Further in accordance with a preferred embodiment there is provided apparatus for hemostasis of an artery having a puncture after arterial catheterization, the apparatus including:

an hemostasis catheter including an inflatable anchor at a forward end thereof and a balloon adjacent the forward end thereof and spaced from the inflatable anchor, the hemostasis catheter being constructed such that inflation of the balloon adjacent the forward end of the hemostasis catheter in engagement with an outer wall surface of the artery causes the forward end of the hemostasis catheter to be withdrawn completely from the wall of the artery and spaced therefrom.

Preferably, the forward edge of the hemostasis catheter extends forwardly less than the extent of the balloon when inflated. In accordance with a preferred embodiment of the present invention, the forward edge of the hemostasis catheter extends less than 4 mm beyond the forward edge of the balloon when not inflated.

BRIEF DESCRIPTION OF THE DRAWINGS

The present invention will be understood and appreciated more fully from the following detailed description, taken in conjunction with the drawings in which:

FIGS. 1–10 are simplified illustrations of a method and apparatus for hemostasis following arterial catheterization, in accordance with a preferred embodiment of the present invention employing a novel catheter introducer, wherein:

FIGS. 1A and 1B are illustrations of insertion of a catheter introducer into an artery;

FIG. 2 is an illustration of the catheter introducer and an associated catheter during arterial catheterization;

FIG. 3 is an illustration of the catheter introducer following removal of the catheter used during arterial catheterization;

FIG. 4 is an illustration of introduction of an inflatable anchor into the artery;

FIG. 5 is an illustration of inflation of the inflatable anchor;

FIG. 6 is an illustration of retraction of the inflated inflatable anchor into engagement with the forward end of the catheter introducer;

FIG. 7 is an illustration of retraction of the catheter introducer by retraction of the inflatable anchor such that the inflated inflatable anchor lies against an inner wall surface of a wall of the artery;

FIG. 8 is an illustration of inflation of a balloon adjacent the forward end of the catheter introducer such that the forward end of the catheter introducer is retracted and spaced from an outer wall surface of the wall of the artery and blood flow out of the artery is prevented by the inflated balloon;

FIG. 9 is an illustration of the arrangement of FIG. 8, following deflation and removal of the inflatable anchor;

FIG. 10 is an illustration of injection of a hemostatic agent following the step illustrated in FIG. 9;

FIGS. 11–20 are simplified illustrations of a method and apparatus for hemostasis following arterial catheterization, in accordance with another preferred embodiment of the present invention employing a novel catheter, wherein:

FIG. 11 is an illustration of insertion of a catheter introducer into an artery as known in the prior art;

FIG. 12 is an illustration of the catheter introducer and an associated catheter during arterial catheterization as known in the prior art;

FIG. 13 is an illustration of the catheter introducer following removal of the catheter used during arterial catheterization as known in the prior art;

FIG. 14 is an illustration of introduction of a hemostasis catheter into the artery;

FIG. 15 is an illustration of inflation of an inflatable anchor in hemostasis catheter;

FIG. 16 is an illustration of retraction of the hemostasis catheter into engagement with the forward end of the catheter introducer;

FIG. 17 is an illustration of retraction of the hemostasis catheter such that the inflated inflatable anchor lies against an inner wall surface of a wall of the artery;

FIG. 18 is an illustration of retraction of the catheter introducer from the vicinity of the artery;

FIG. 19 is an illustration of partial inflation of a balloon adjacent the forward end of the hemostasis catheter such that blood flow out of the artery is prevented by the inflated balloon;

FIG. 20 is an illustration of deflation of the inflatable anchor following the step of FIG. 19;

DETAILED DESCRIPTION OF PREFERRED EMBODIMENTS

Figure 2:
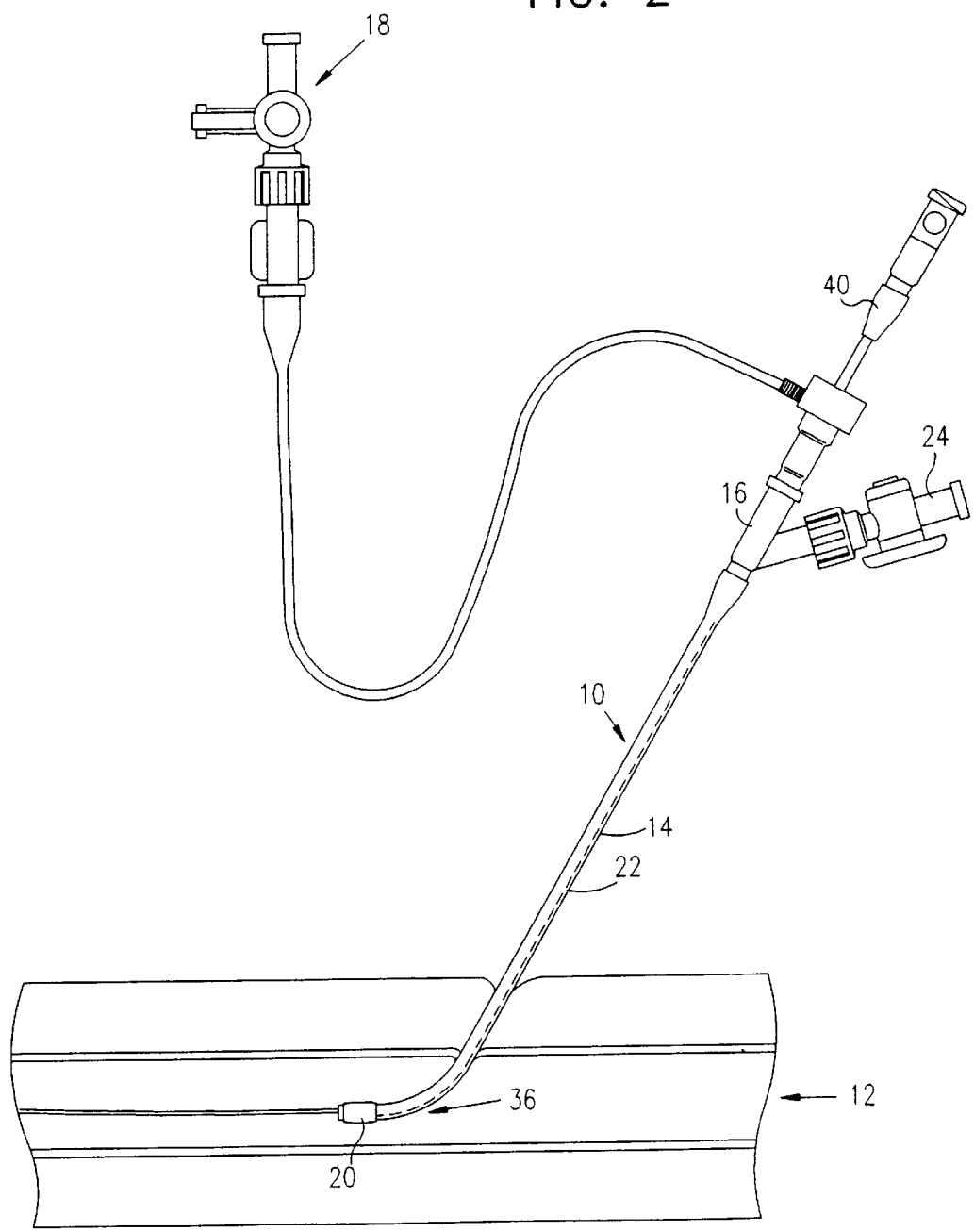

Reference is now made to FIGS. 1–10, which are simplified illustrations of a method and apparatus for hemostasis following arterial catheterization, in accordance with a preferred embodiment of the present invention employing a novel catheter introducer.

FIG. 1A illustrates insertion of a catheter introducer 10 constructed and operative in accordance with a preferred embodiment of the present invention into an artery 12. The catheter introducer 10 is generally similar to conventional catheter introducers in that it incorporates a sheath 14 and a catheter head 16 which is coupled to a pressure gauge 18 which is conventionally employed for blood pressure monitoring.

In accordance with a preferred embodiment of the present invention, a peripheral inflatable balloon 20 is formed adjacent the forward end 21 of sheath 14 and communicates via a lumen 22 formed within sheath 14 and an inflation fluid controlling valve assembly 24 with a source of pressurized inflating fluid (not shown). A typical fluid interconnection between the balloon 20 and the lumen 22 may be seen clearly in FIG. 1B, which is an enlarged portion of FIG. 1A, and indicated by reference numeral 26.

Preferably, the catheter introducer is inserted into the artery following earlier insertion of a guide wire 28 via a hypodermic needle. The catheter introducer 10 is slid along the guide wire 28 along with an intermediate sheath 30 having a tapered forward end 32 and a head 34. Once the catheter introducer 10 is positioned with its forward end well inside the artery, the guide wire 28 and the intermediate sheath 30 are removed.

Referring now to FIG. 2, there is shown the catheter introducer 10 and an associated catheter 40 during arterial catheterization. Arterial catheterization takes place in an entirely conventional manner.

Figure 3:
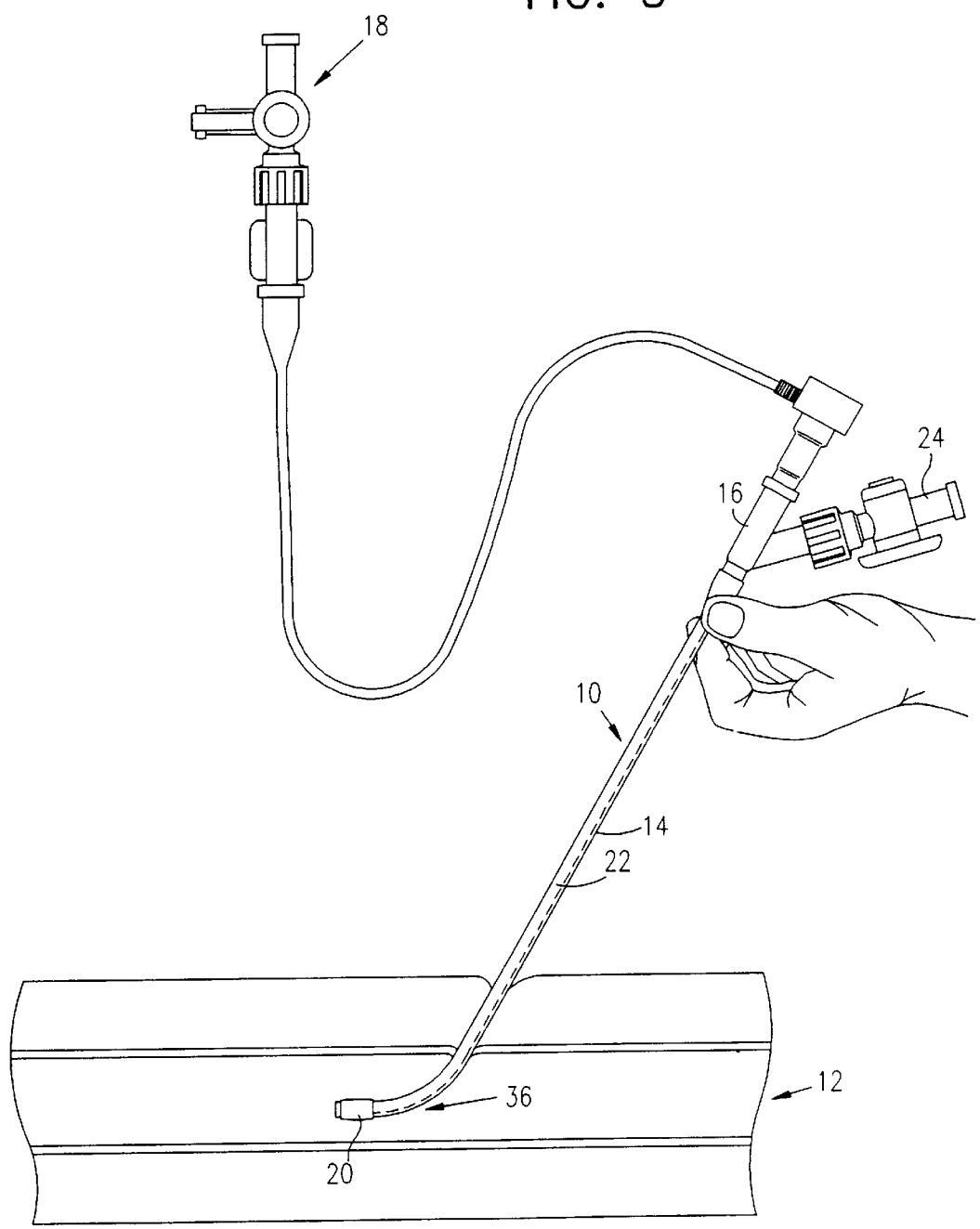

Reference is now made to FIG. 3, which is an illustration of the catheter introducer following removal of the catheter used during arterial catheterization. It is seen that the forward end 32 of the catheter introducer 10 remains within the artery and that the balloon 20 is not inflated.

The remainder of the description hereinbelow relating to FIGS. 4–10 deals with removal of the catheter introducer in accordance with a preferred embodiment of the present invention.

Figure 4:
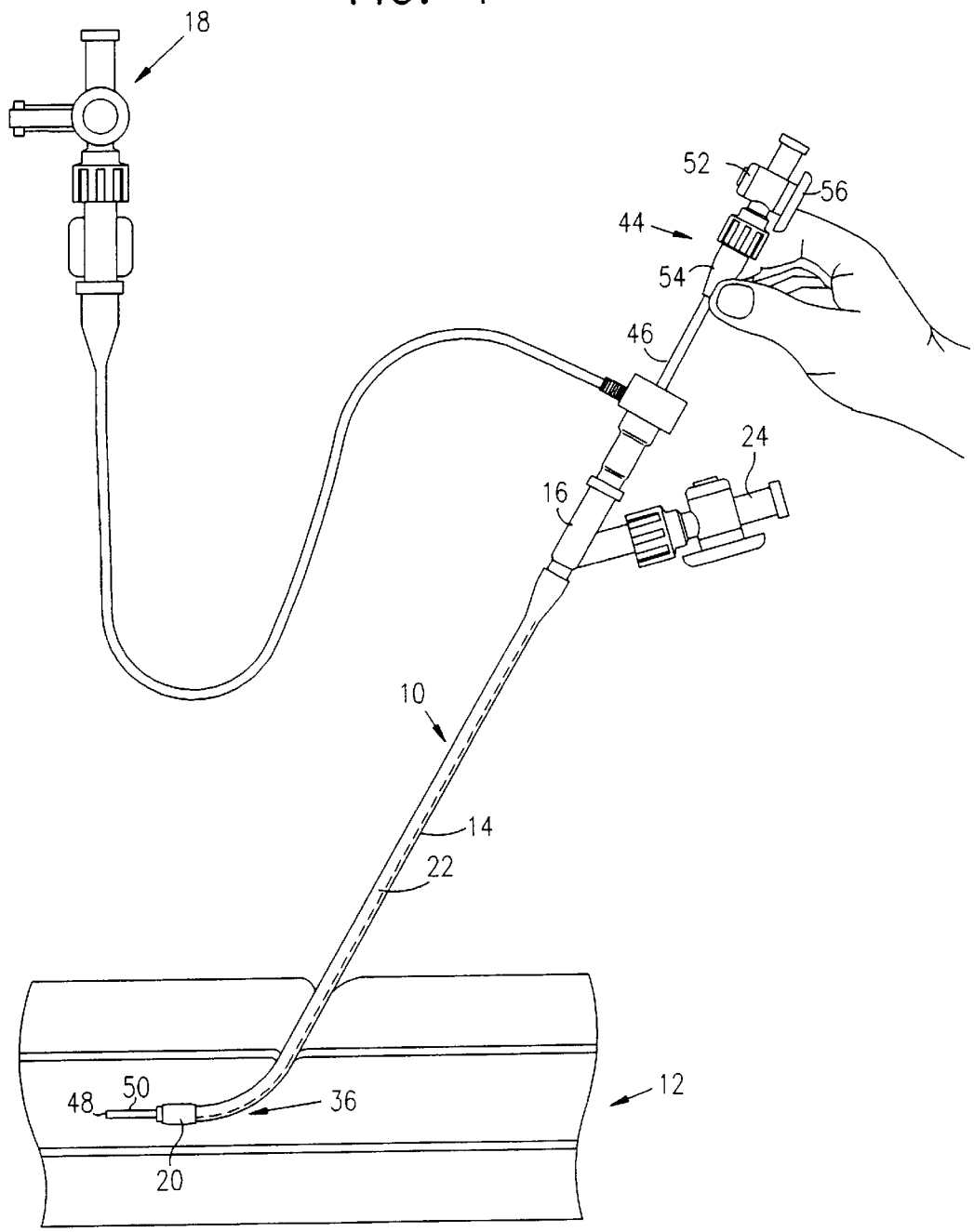

FIG. 4 illustrates introduction of an inflatable anchor assembly 44 into the artery 12. The inflatable anchor assembly 44 comprises a sheath 46 having an inflatable anchor balloon 48 mounted at a forward end 50 thereof and a head 52 mounted at an opposite end 54 of the sheath 46 and having a manually controllable valve 56 mounted thereon.

Figure 5:
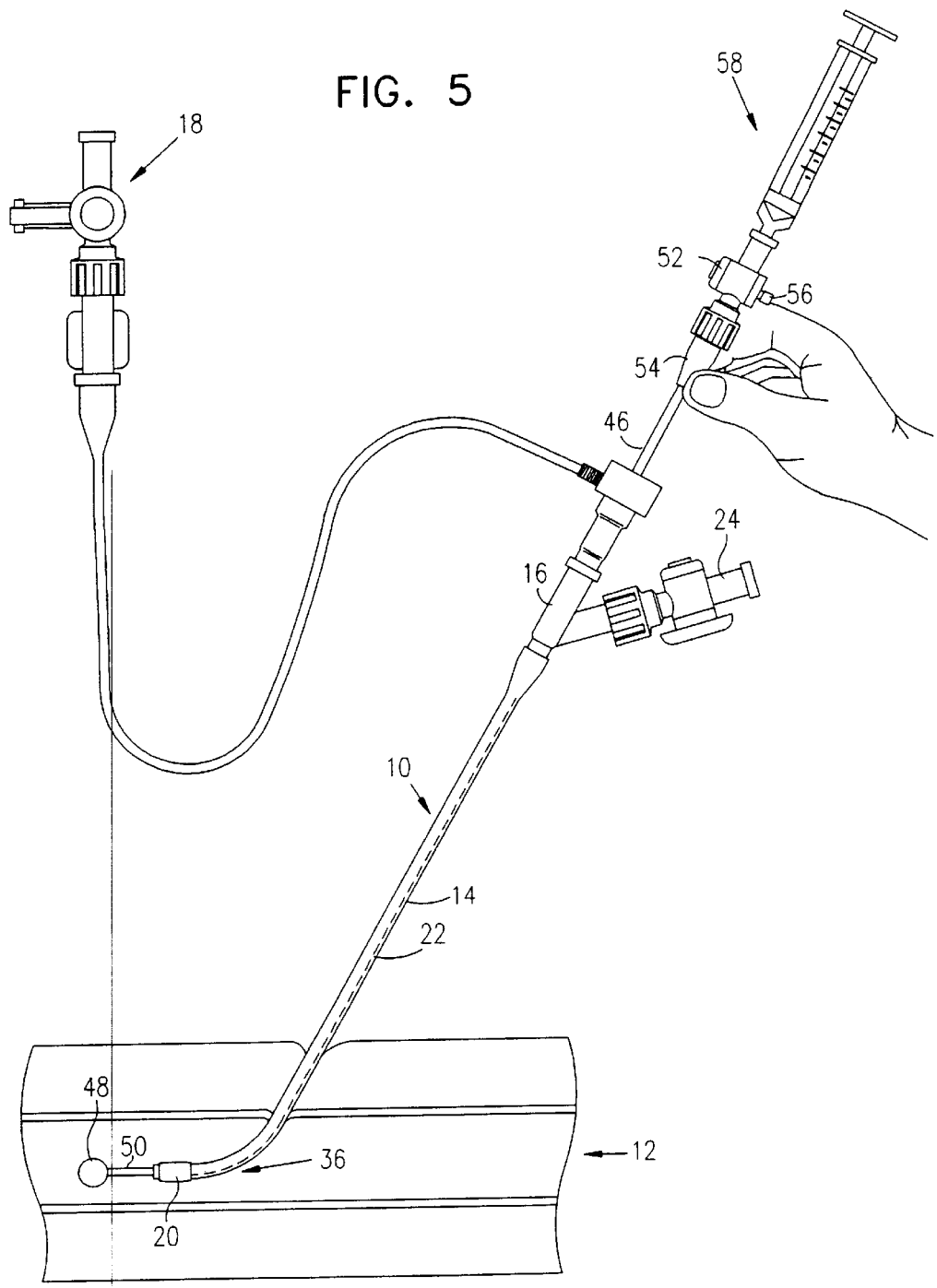
Figure 6:
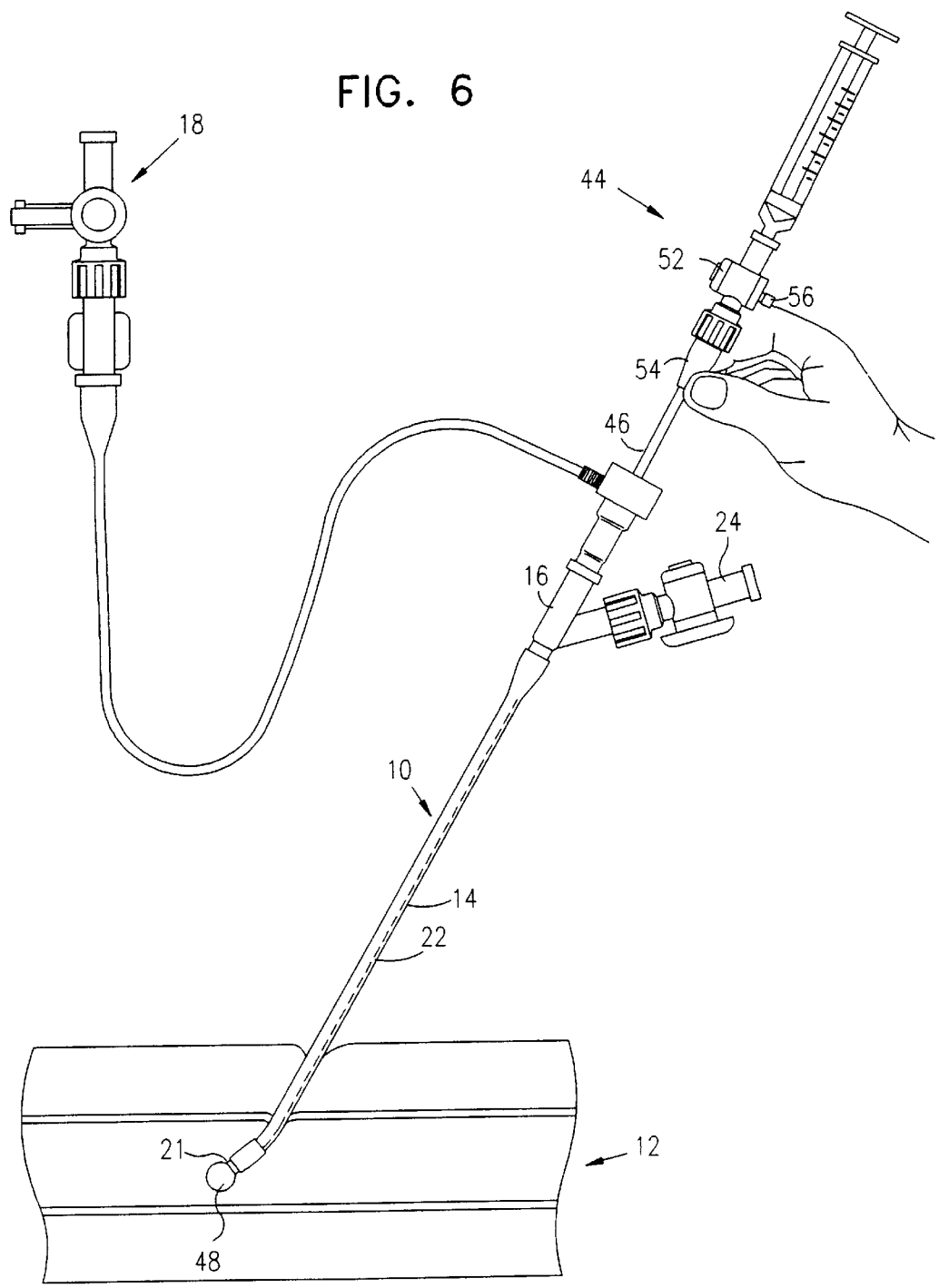

As seen in FIG. 5, the inflatable anchor balloon 48 is inflated within artery 12 by means of a fluid introduced into the sheath, as by a syringe 58 coupled to head 52 via valve 56. Following inflation of the anchor balloon 48, the entire inflatable anchor assembly 44 is preferably retracted such that the inflated balloon 48 abuts against the forward end 21 of the catheter introducer 10, as seen in FIG. 6.

Figure 7:
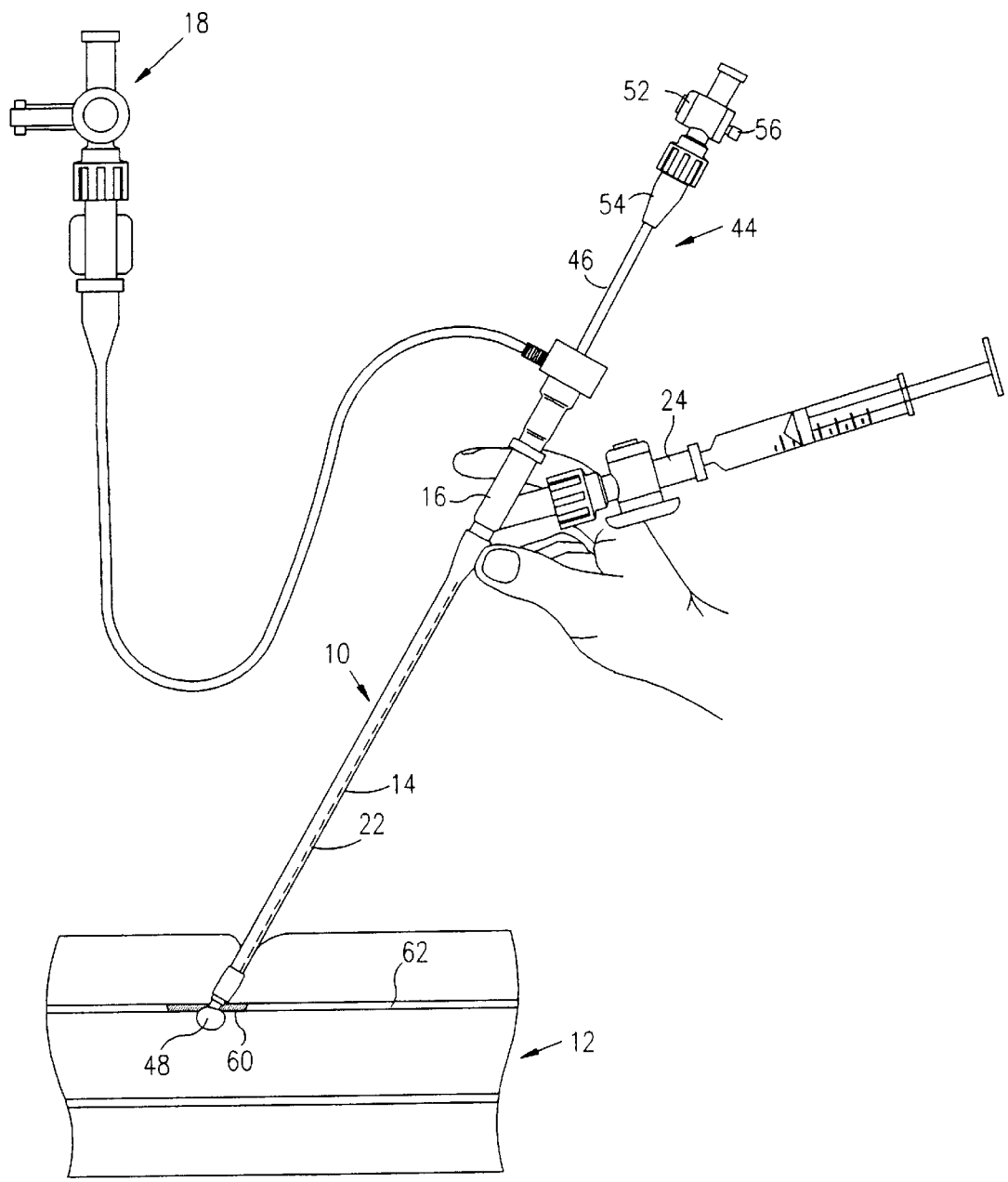

The inflatable anchor assembly 44 is further retracted, as shown in FIG. 7, thus also retracting the catheter introducer 10 due to the engagement of the inflated balloon 48 against the forward end 21 of the catheter introducer 10. This retraction preferably proceeds until the inflated inflatable anchor balloon 48 lies against an inner wall surface 60 of a wall 62 of the artery 12.

Figure 8:
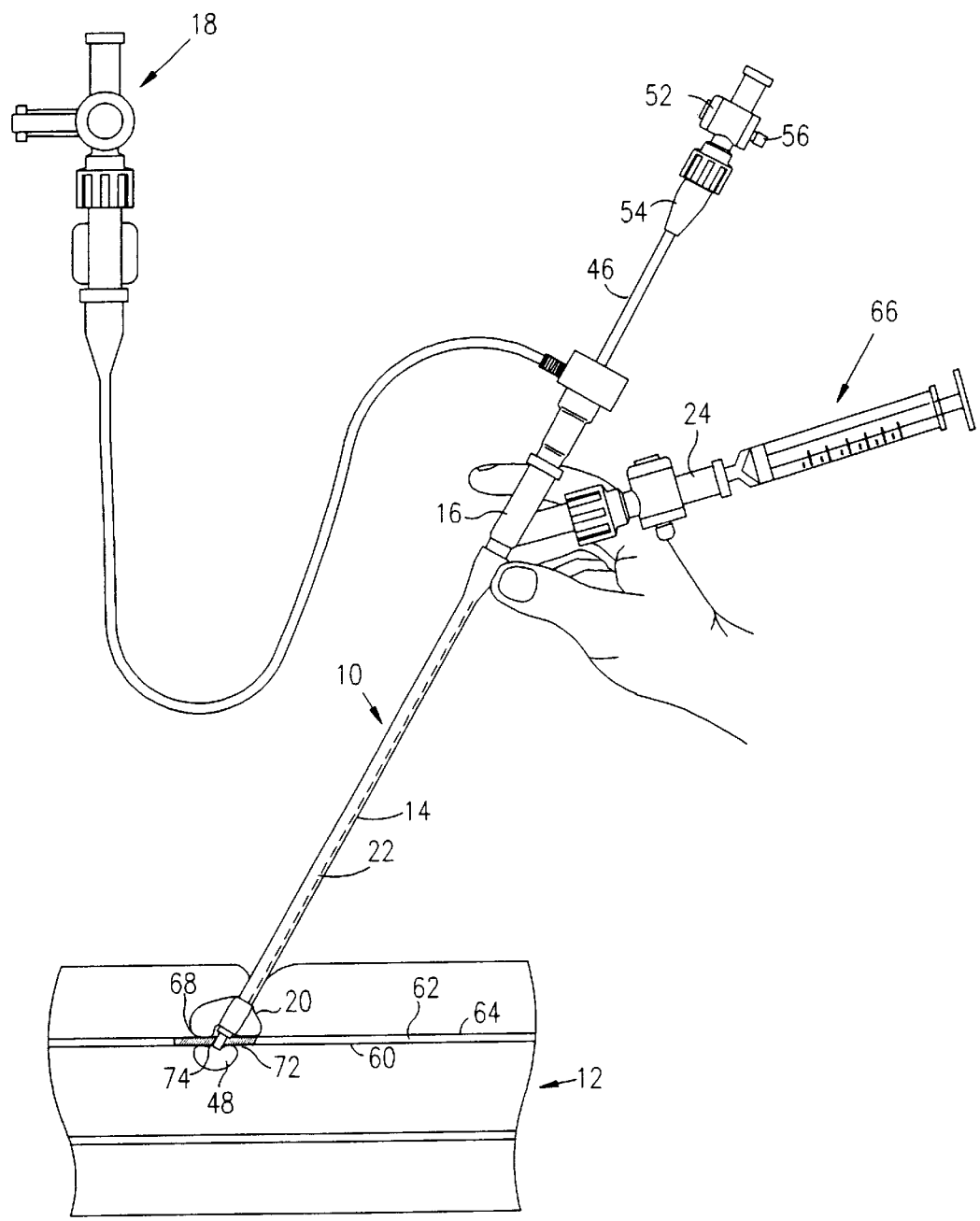

FIG. 8 is an illustration of inflation of balloon 20 adjacent the forward end 21 of the catheter introducer 10 such that the forward end 21 of the catheter introducer 10 is retracted and spaced from an outer wall surface 64 of the wall 62 of the artery 12 and blood flow out of the artery is prevented by the inflated balloon 20. Inflation of balloon 20 adjacent the wall surface 64 is preferably achieved using a syringe 66 associated with valve assembly 24.

It is a particular feature of the present invention that the placement of balloon 20 relative to the forward end 21 of the catheter introducer is such that when the balloon 20 is fully inflated, as shown in FIG. 8, the forward facing outer surface 68 of the balloon 20 lies forward of the forward end 21 of the catheter introducer 10 and thus, due to engagement of the surface 68 with an outer wall surface 64 of artery 12, retracts the forward end 21 of the catheter introducer out of engagement with the wall 62 of artery 12. At the same time the flexibility of inflated anchor balloon 48 enables it to move somewhat forwardly, such that an artery facing surface 72 thereof tightly engages the inner wall surface 60 of artery 12, while the outer wall surface 64 thereof is at the same time tightly engaged by forward facing outer surface 68 of balloon 20.

Figure 9:
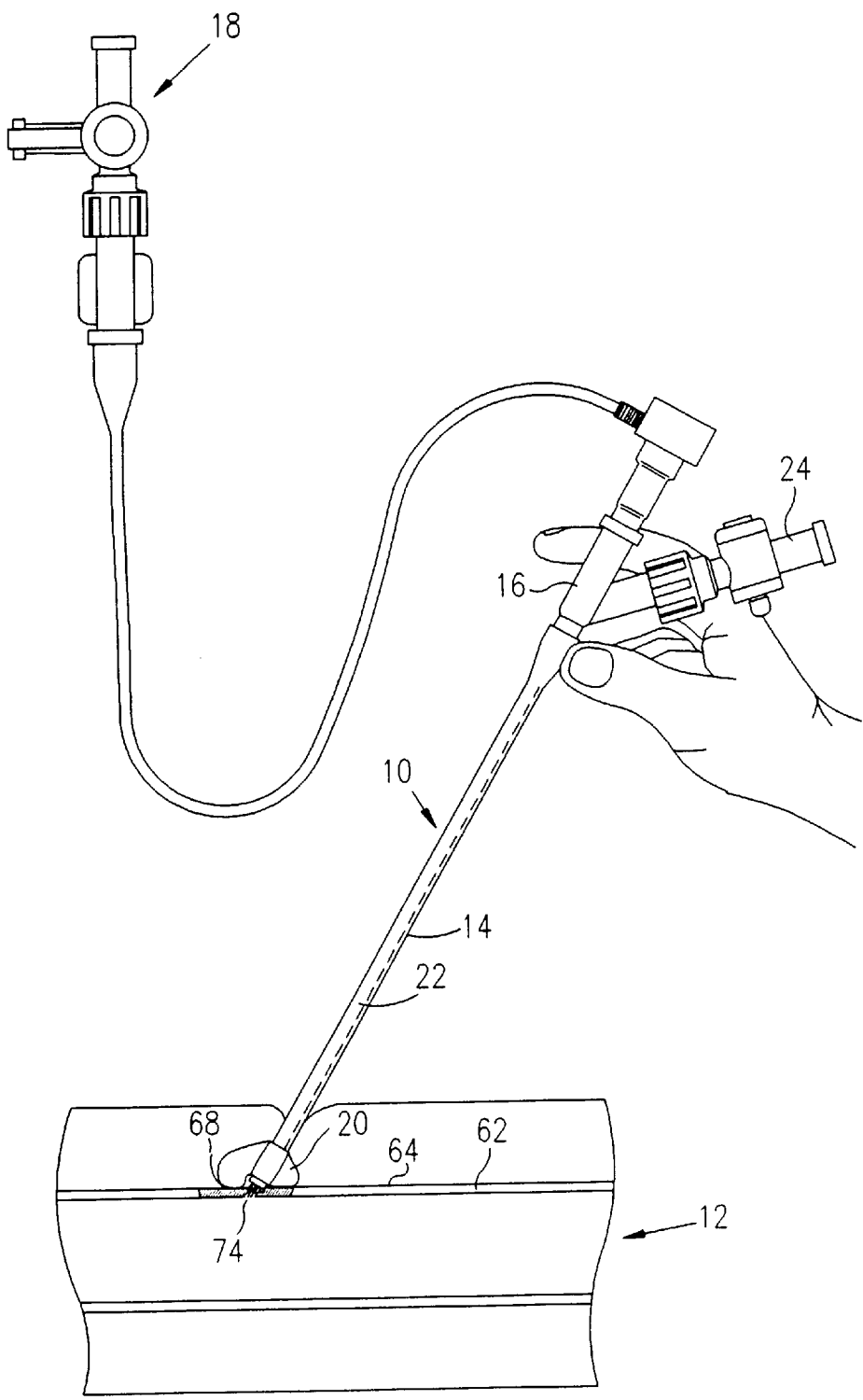
Figure 10:
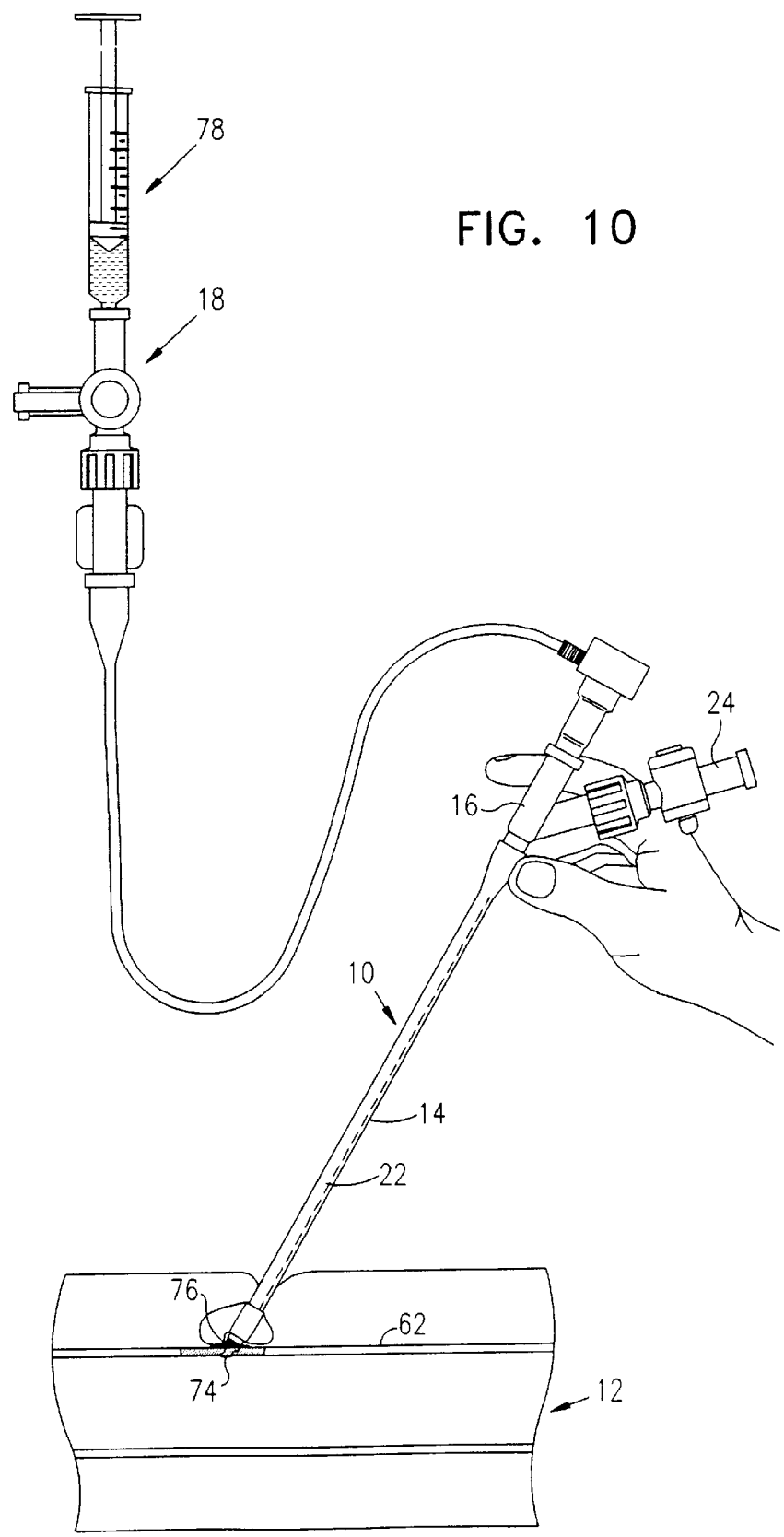

The resulting sealing arrangement enables hemostasis to occur at the aperture 74 formed in wall 62 of artery 12. Following sufficient hemostasis the anchor balloon 48 is deflated and the anchor assembly 44 is removed. FIG. 9 is an illustration of the arrangement of FIG. 8, following deflation and removal of the inflatable anchor assembly 44. optionally, as illustrated in FIG. 10, a hemostatic agent 76 may be injected via the catheter introducer 10 to a location adjacent aperture 74 but outside the artery 12. This injection may employ a syringe 78 which may be coupled via head 16 or alternatively via (pressure gauge) 18.

Reference is now made to FIGS. 11–22, which are simplified illustrations of a method and apparatus for hemostasis following arterial catheterization, in accordance with another preferred embodiment of the present invention employing a novel hemostasis catheter.

Figure 11:
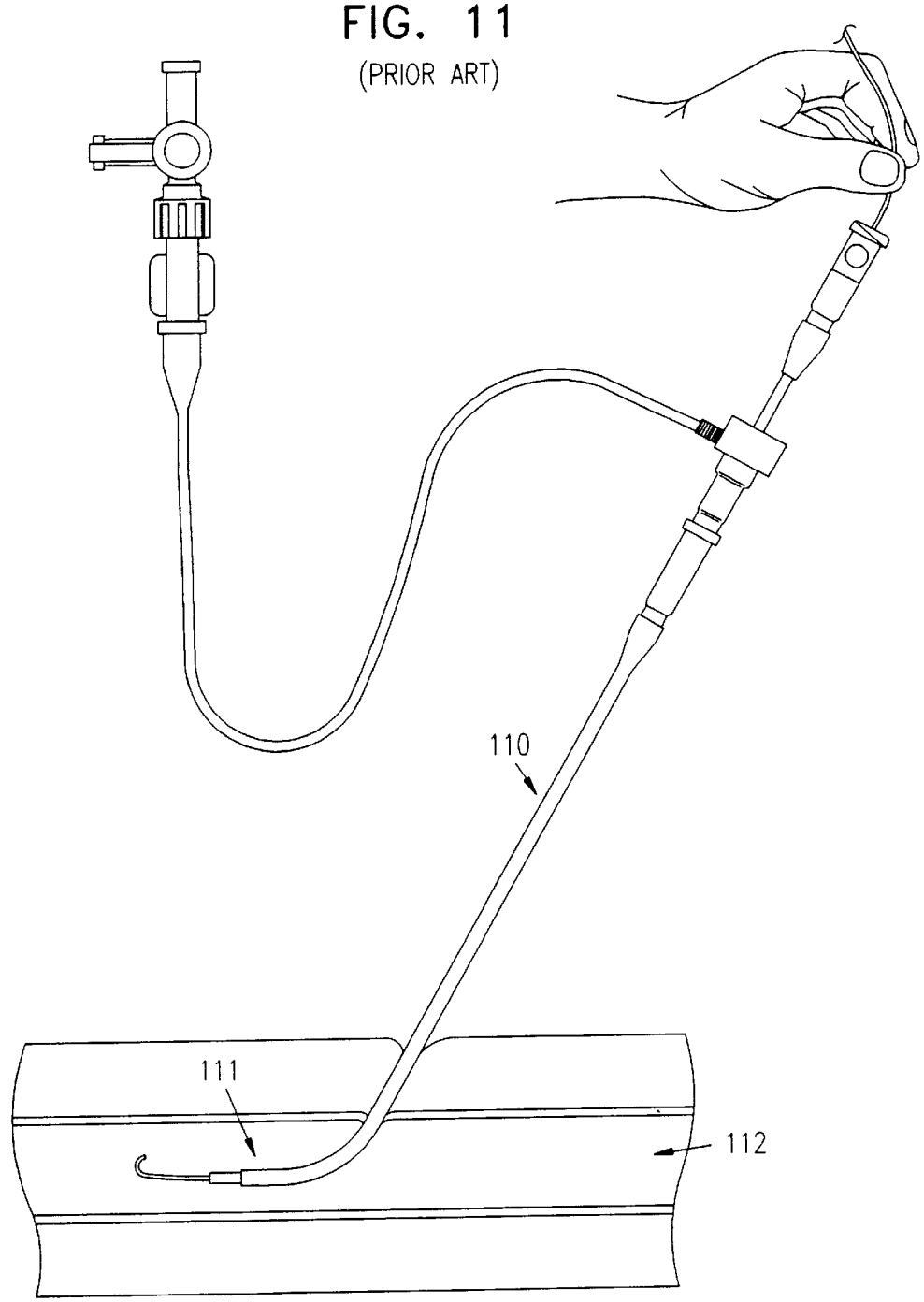
Figure 12:
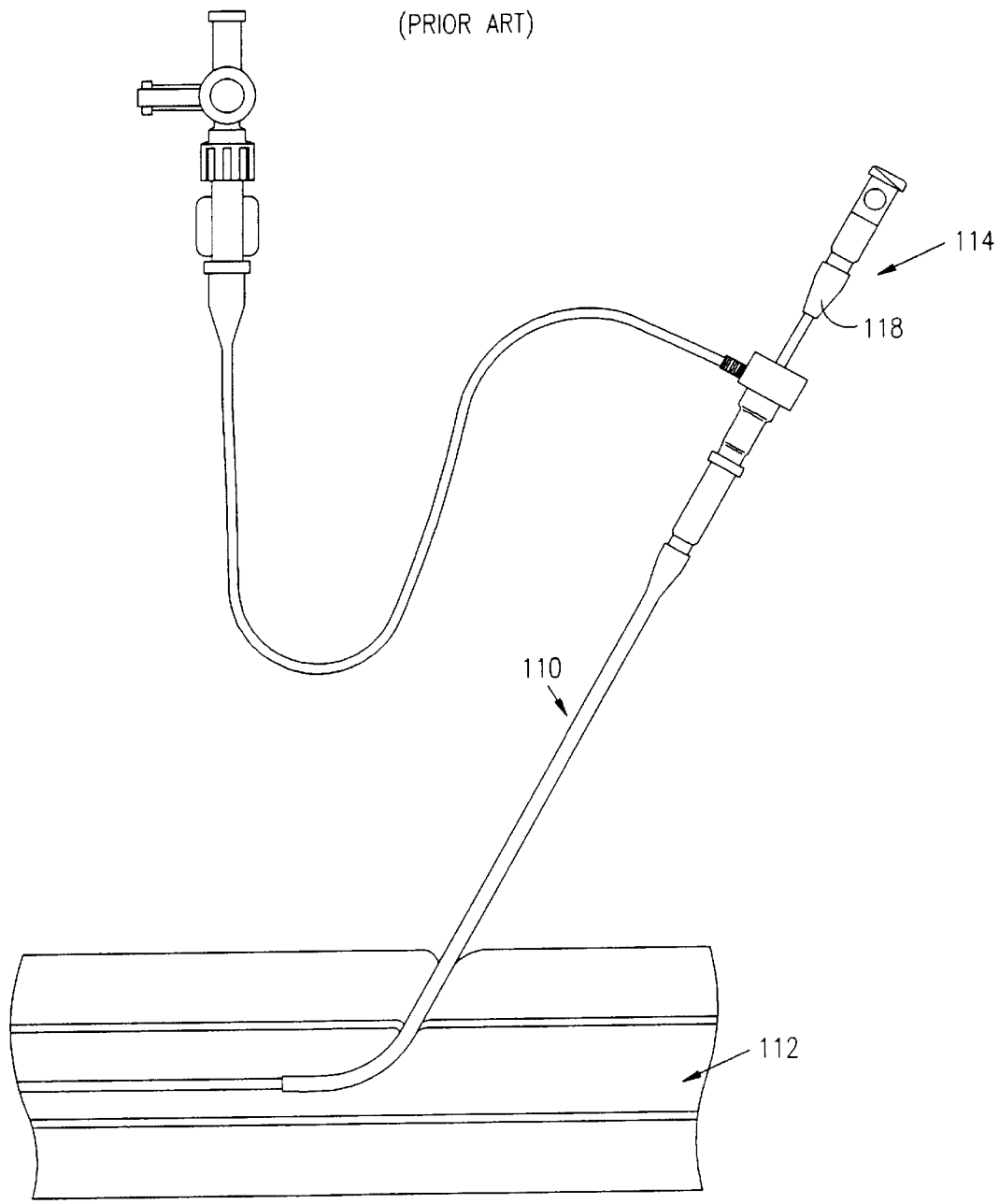
Figure 13:
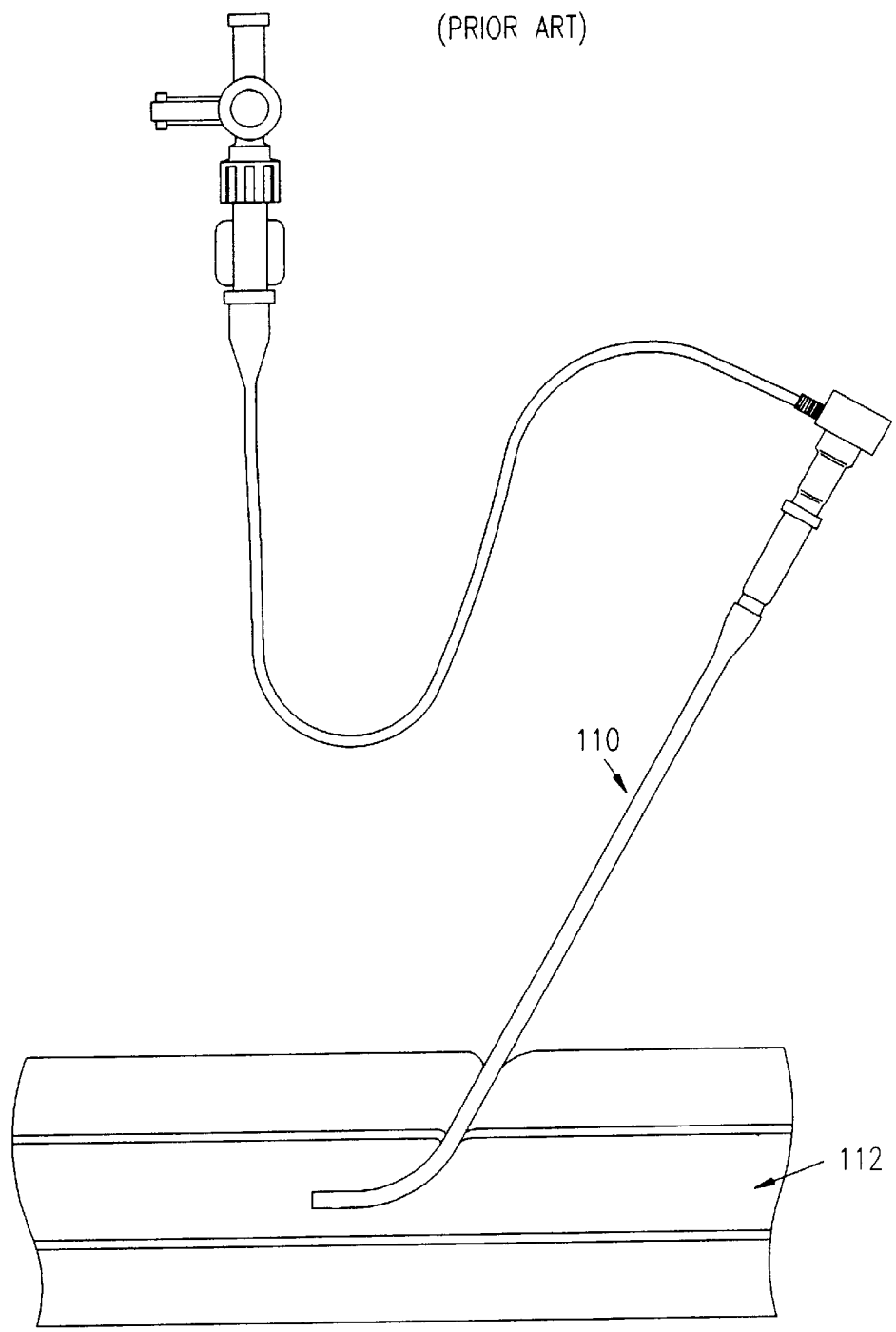

The method and apparatus of FIGS. 11–22 employs a conventional catheter introducer 110 having a forward end 111, which is introduced into an artery 112 in an entirely conventional manner, as well known in the prior art, and shown in FIG. 11. Arterial catheterization is also carried out in an entirely conventional manner using a conventional catheter 114, as shown in FIG. 12. Following removal of the catheter 114, the conventional catheter introducer 110 remains in the artery 112 as illustrated in FIG. 13 and well known in the prior art.

Figure 14:
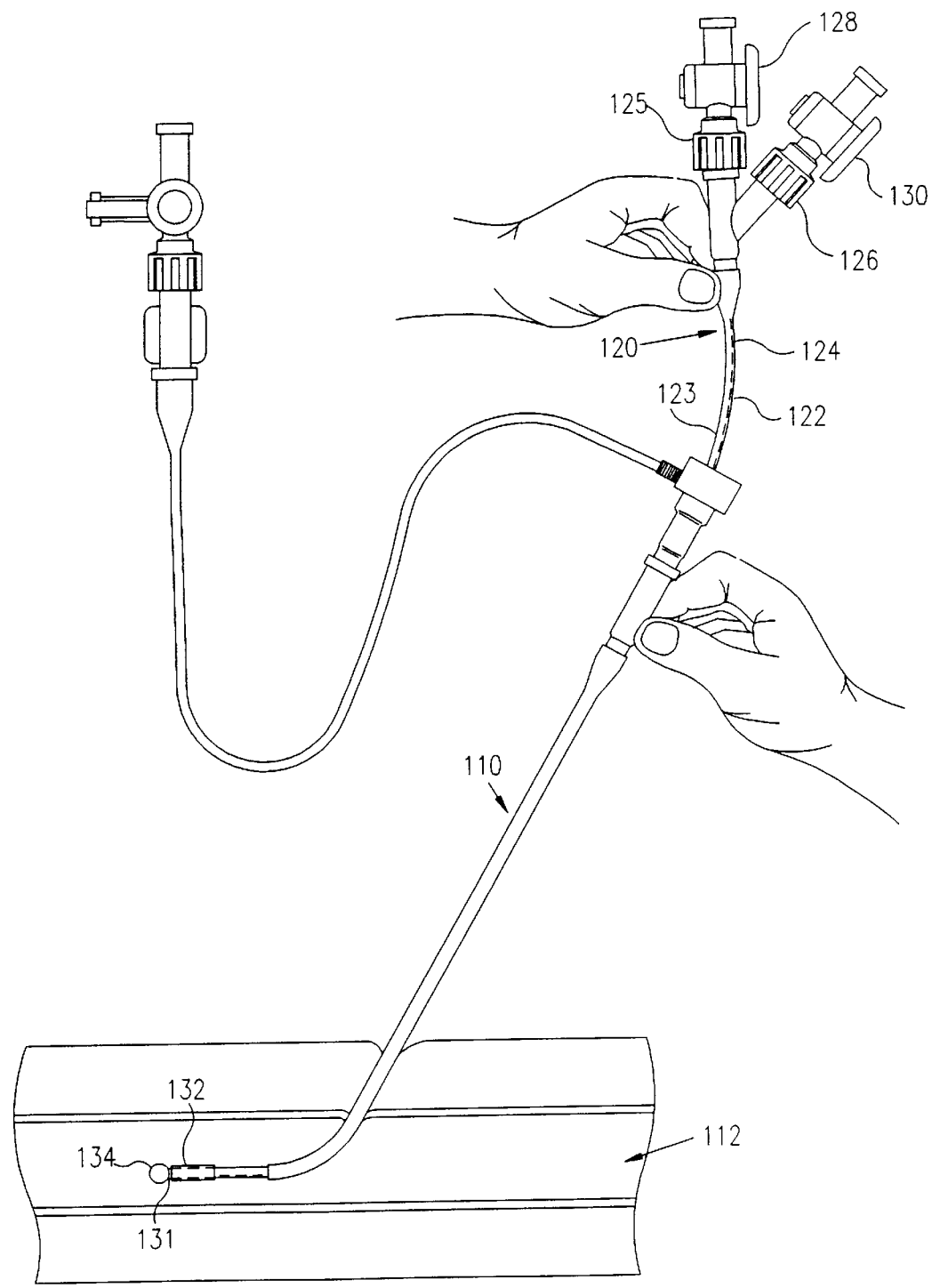

At this stage, as shown in FIG. 14, a hemostasis catheter 120, constructed and operative in accordance with a preferred embodiment of the present invention, is introduced into the artery 112 via the catheter introducer 110. The hemostasis catheter 120 comprises a sheath 122 having first and second lumens 123 and 124 having a pair of heads 125 and 126, associated with respective valves 128 and 130. Adjacent a forward end 131 thereof, there is provided a peripheral balloon 132 and extending forwardly of the forward end 131 there is provided an anchor balloon 134.

Figure 15:
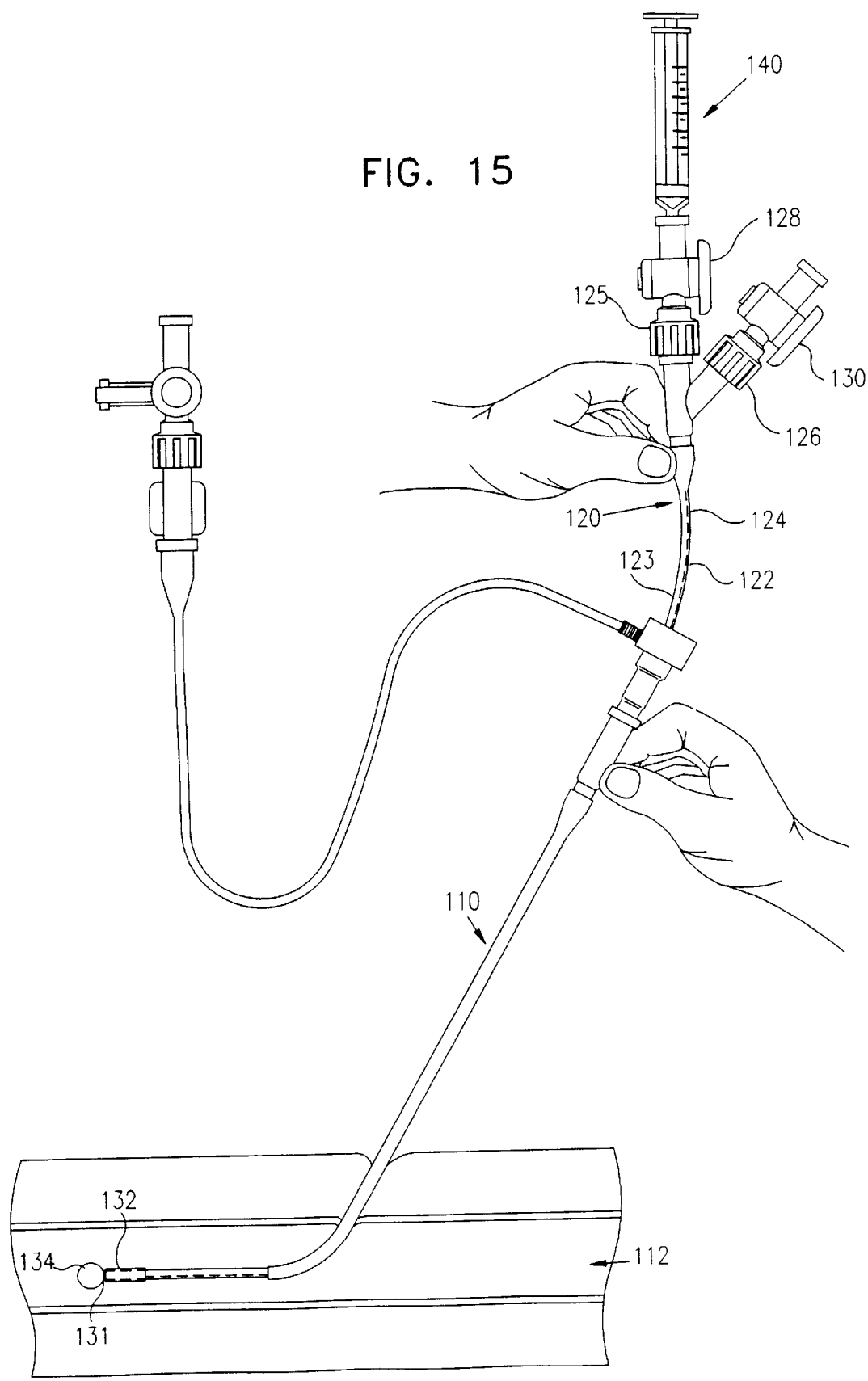

Following introduction of the hemostasis catheter 120, the anchor balloon 134 is inflated within artery 112 as illustrated in FIG. 15, typically by means of a syringe 140 coupled via valve 128, head 125 and lumen 123.

Figure 16:
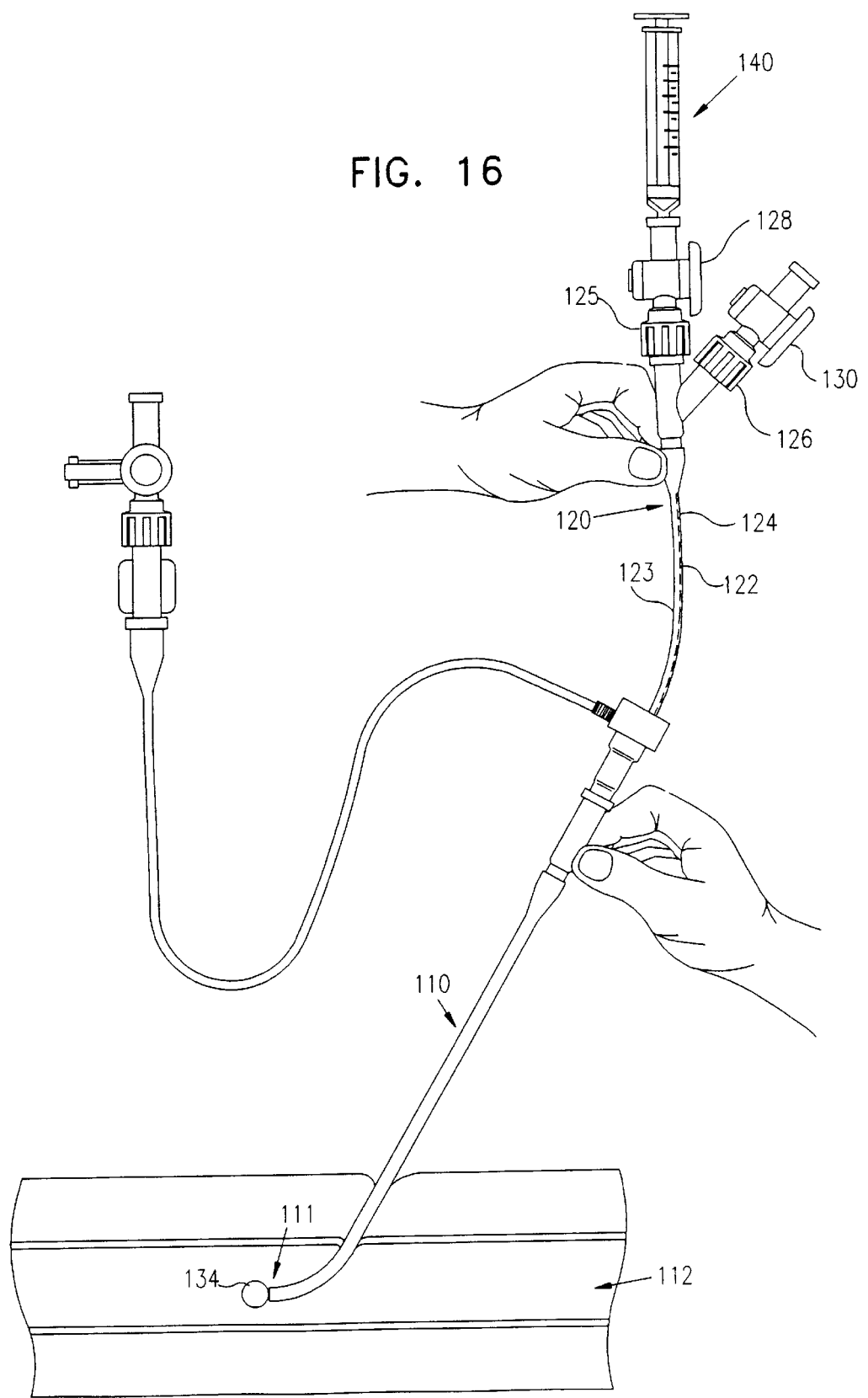

Following inflation of the anchor balloon 134, the entire hemostasis catheter 120 is preferably retracted such that the inflated anchor balloon 134 abuts against the forward end 111 of the catheter introducer 110, as seen in FIG. 16.

Figure 17:
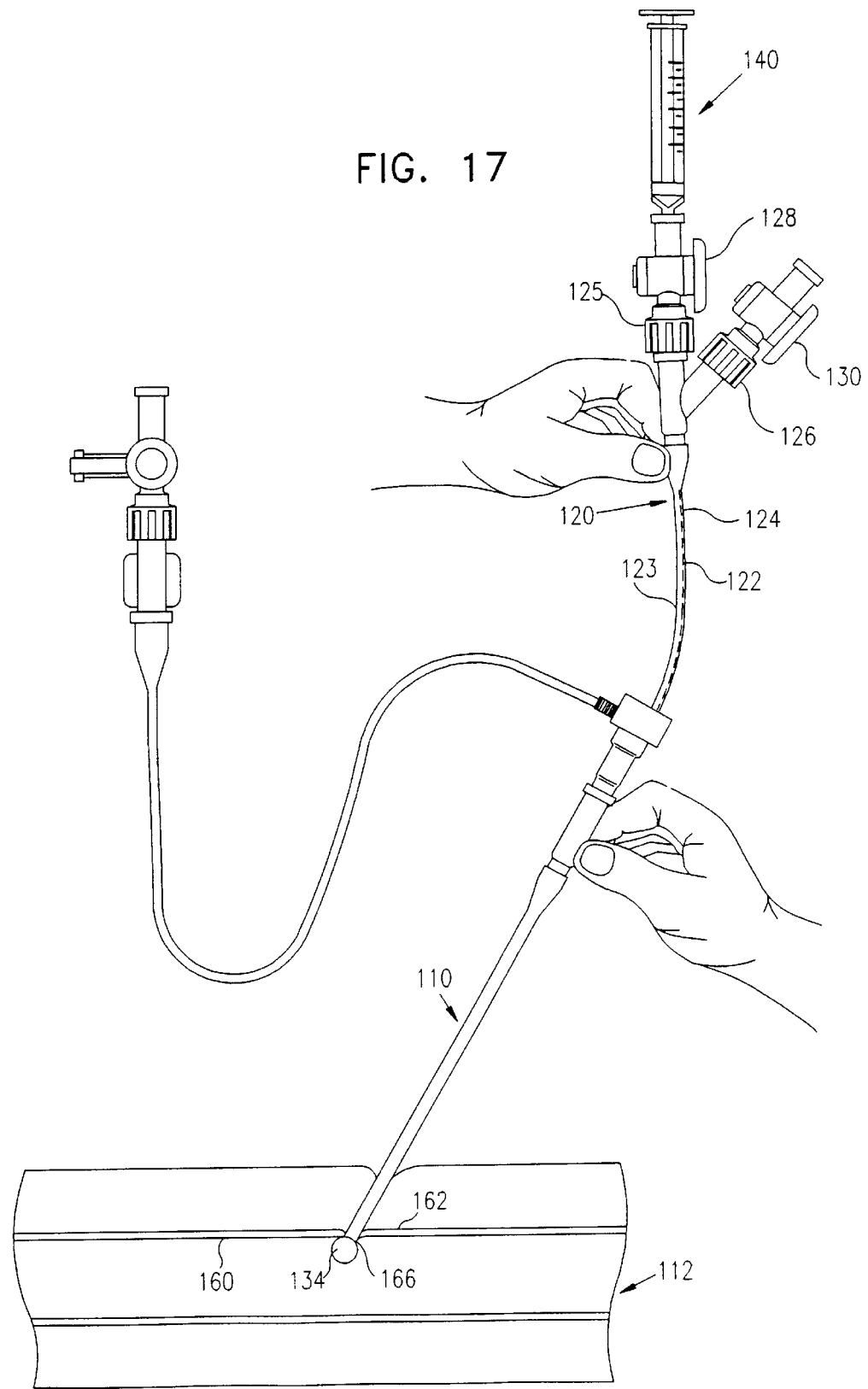

The hemostasis catheter 120 is further retracted, as shown in FIG. 17, thus also retracting the catheter introducer 110 due to the engagement of the inflated anchor balloon 134 against the forward end 111 of the catheter introducer 110. This retraction preferably proceeds until the inflated anchor balloon 134 lies against an inner wall surface 160 of a wall 162 of the artery 112. In this orientation, inflated anchor balloon 134 prevents blood flow through aperture 166 in wall 162.

Figure 18:
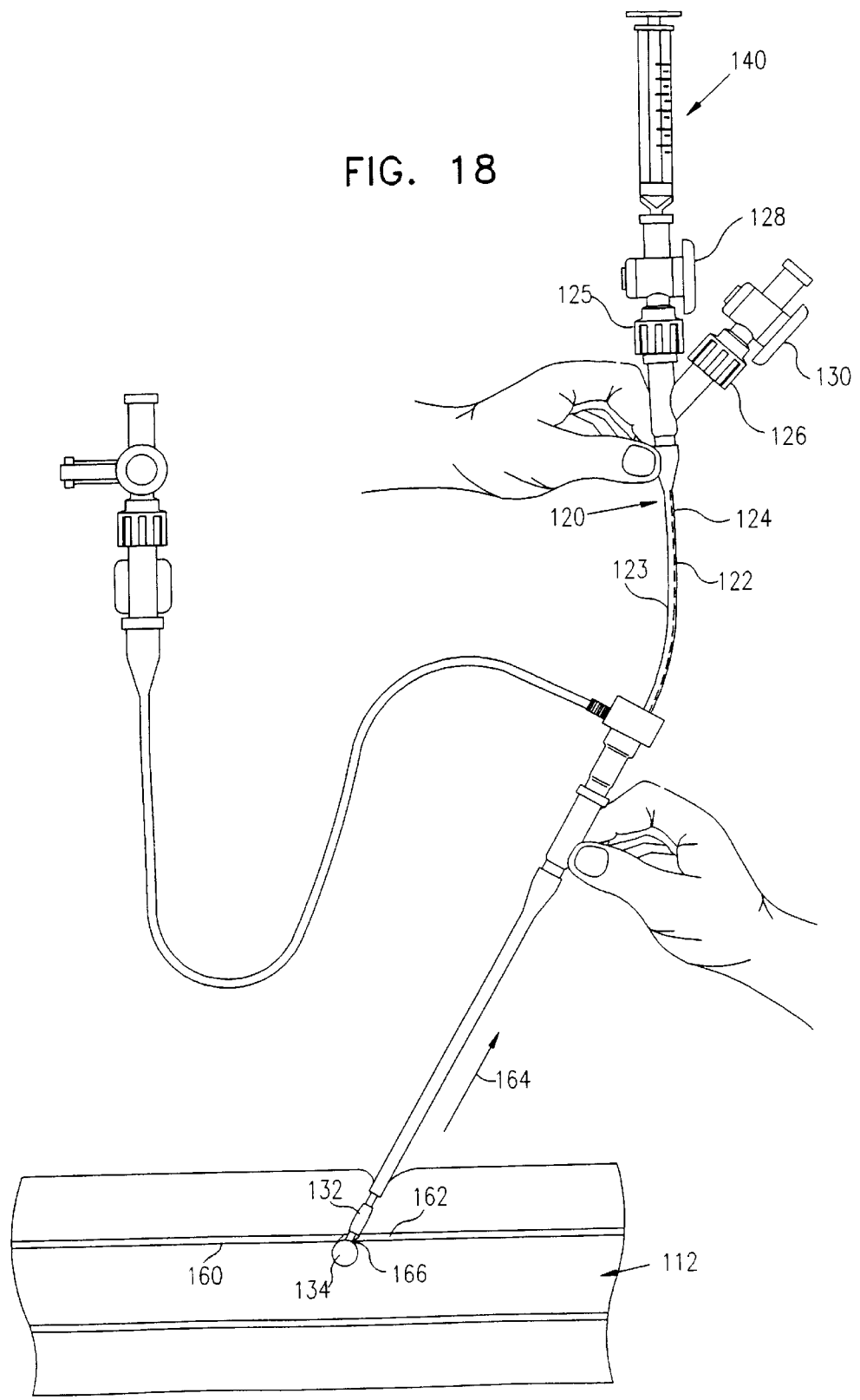

As seen in FIG. 18, the catheter introducer 110 is slightly retracted, as indicated by arrow 164, sufficient to allow peripheral balloon 132 to be inflated, and to bring the forward end 110 of the catheter introducer out of engagement with the artery wall 162, while retaining the forward end 110 within the tissue and in the general vicinity of the aperture 166 in the artery wall 162.

Figure 19:
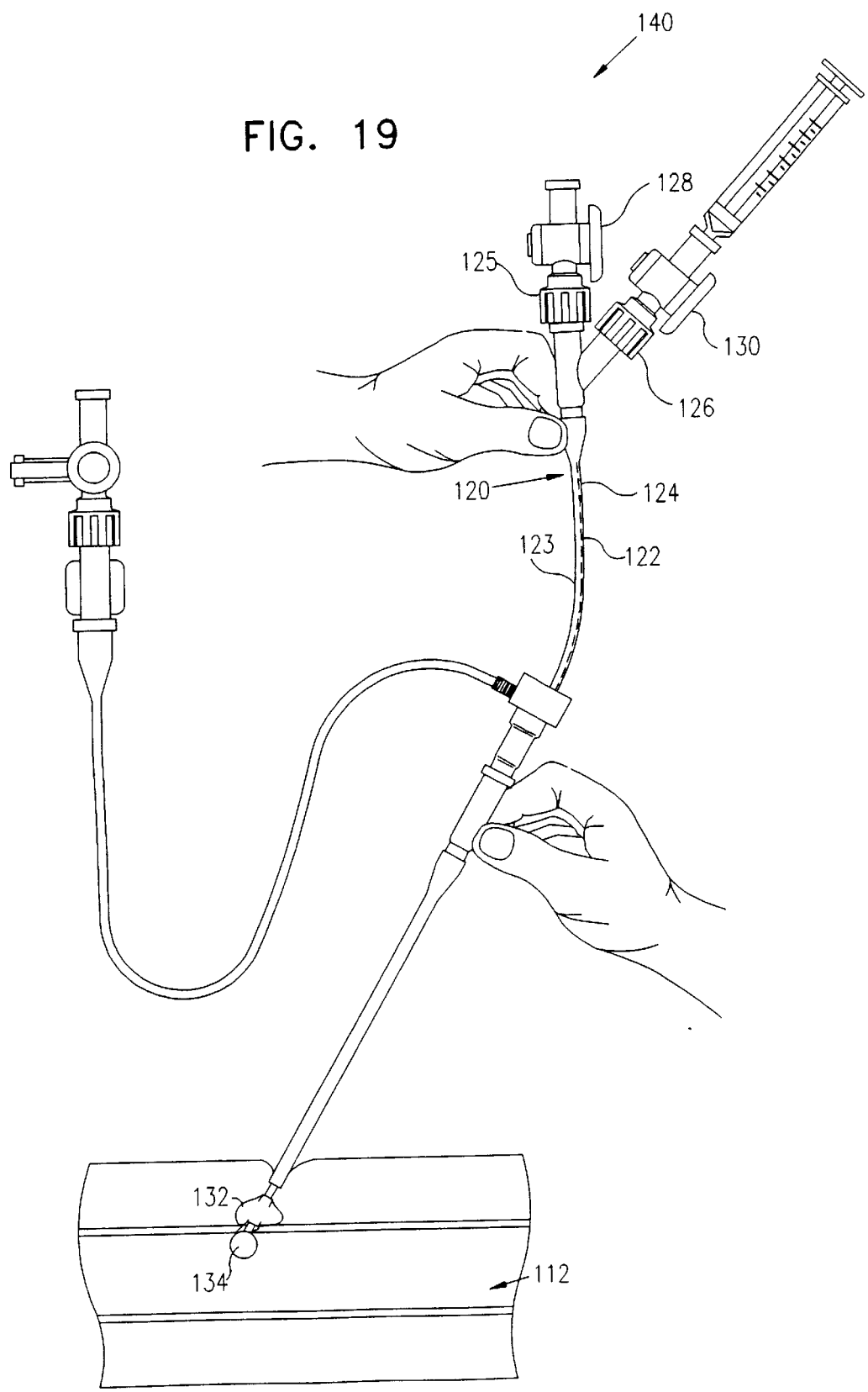

Following the retraction of the catheter introducer 110 illustrated in FIG. 18, the peripheral balloon 132 is partially inflated, as illustrated in FIG. 19. This inflation is preferably effected by means of a syringe 170 coupled via valve 130, head 126 and lumen 124. The partial inflation is preferable such that blood flow out of the artery is prevented by the inflated balloon 132.

Figure 20:
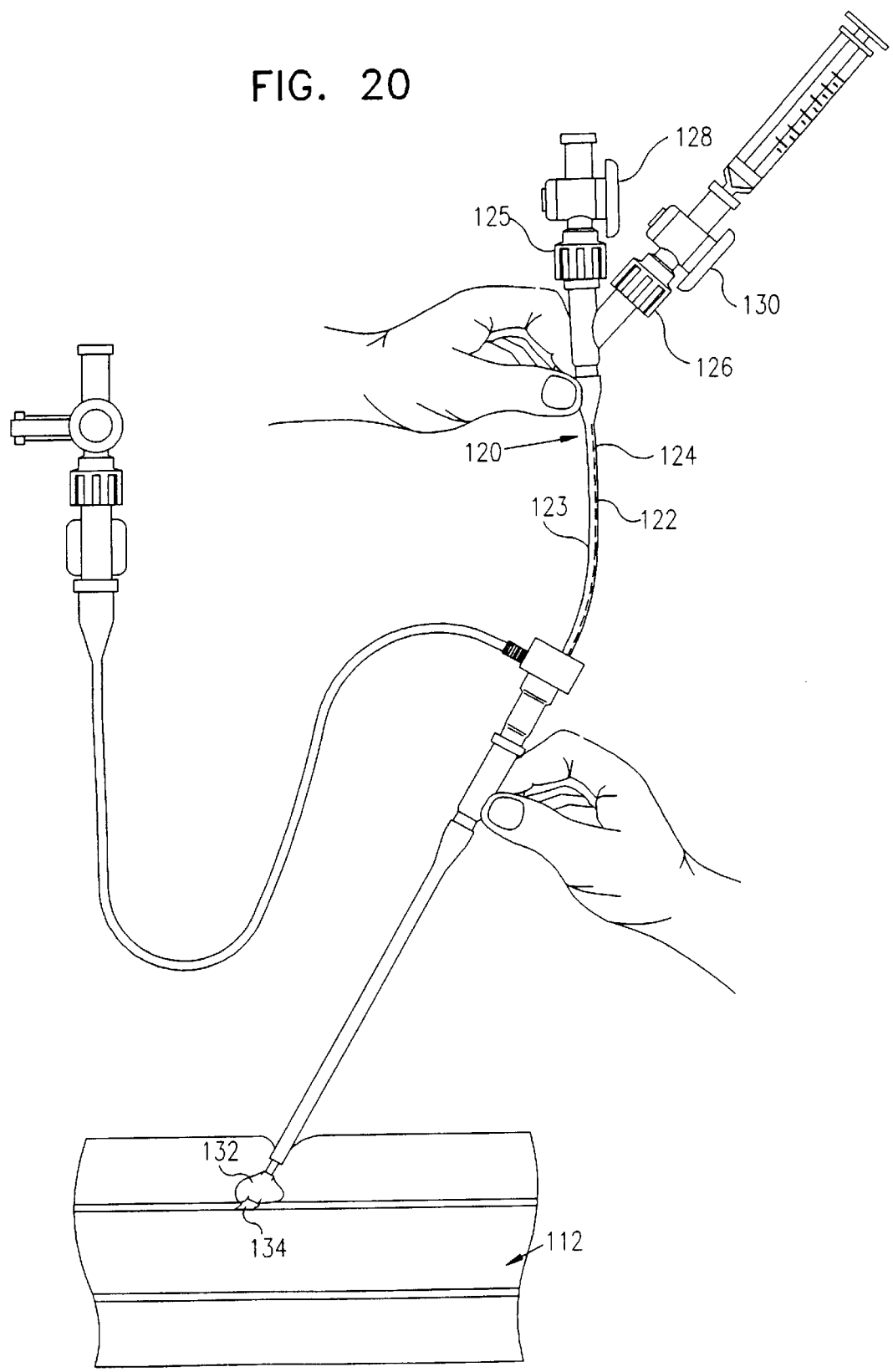

Following the partial inflation illustrated in FIG. 19, the anchor balloon 134 is deflated, as shown in FIG. 20. Following deflation of the anchor balloon 134, the peripheral balloon 132 is further inflated such that the forward end 131 of the hemostasis catheter is retracted and spaced from an outer wall surface of the wall of the artery and blood flow out of the artery is prevented by the inflated balloon 132.

Figure 21:
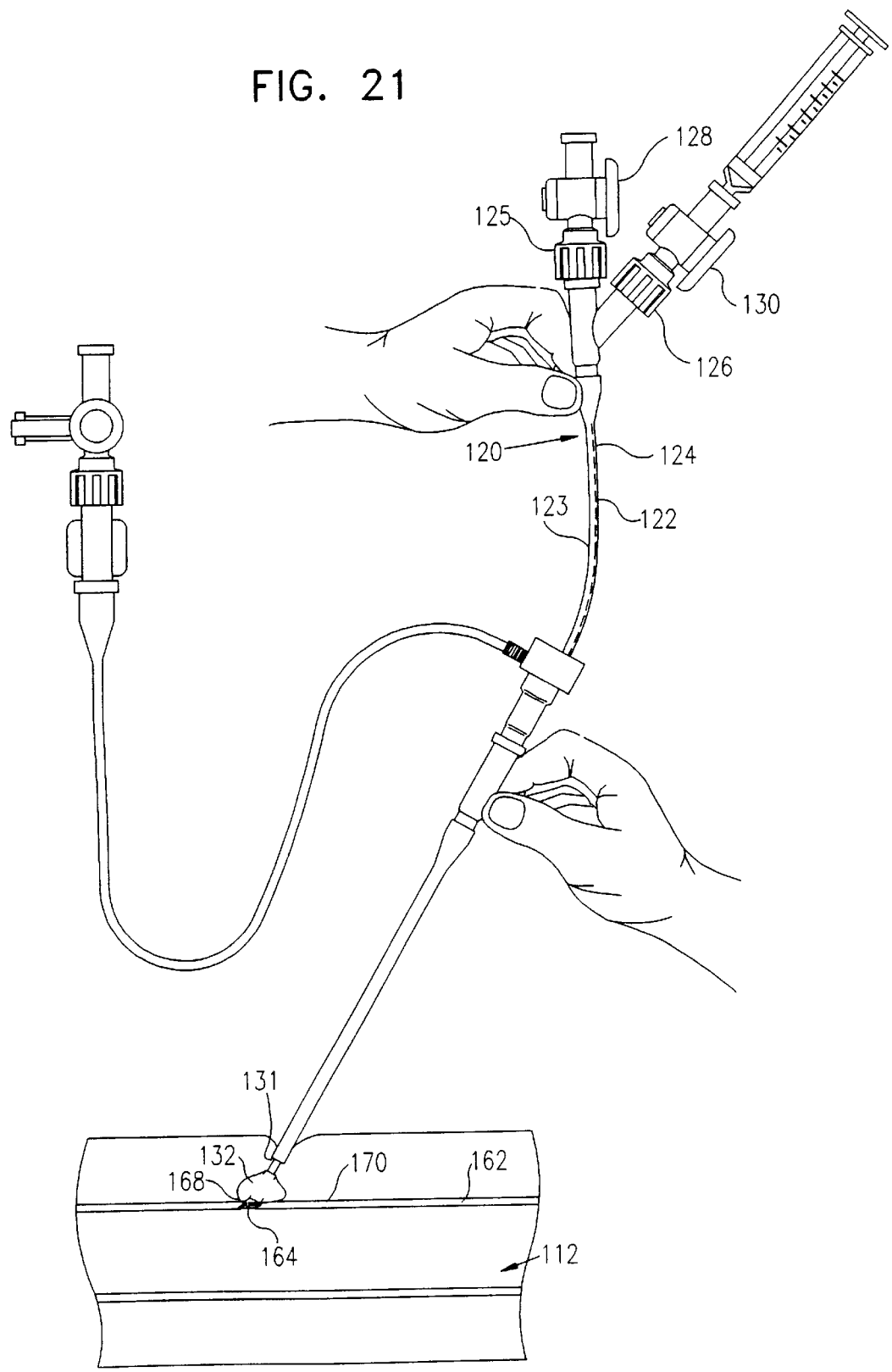
FIG. 21 is an illustration of further inflation of the balloon adjacent the forward end of the hemostasis catheter such that the forward end of the hemostasis catheter is retracted and spaced from an outer wall surface of the wall of the artery and blood flow out of the artery is prevented by the inflated balloon.

It is a particular feature of the present invention that the placement of peripheral balloon 132 relative to the forward end 131 of the hemostasis catheter is such that when the balloon 132 is fully inflated, as shown in FIG. 21, the forward facing outer surface 168 of the balloon 132 lies forward of the forward end 131 of the hemostasis catheter 120 and thus, due to engagement of the surface 168 with an outer wall surface 170 of artery 112, retracts the forward end 131 of the hemostasis catheter out of engagement with the wall 162 of artery 112, while the outer wall surface 170 of the artery is at the same time tightly engaged by forward facing outer surface 168 of balloon 132.

The resulting sealing arrangement enables hemostasis to occur at the aperture 164 formed in wall 162 of artery 112. Following sufficient hemostasis the peripheral balloon 132 is deflated and the hemostasis catheter 120 is removed.

Figure 22:
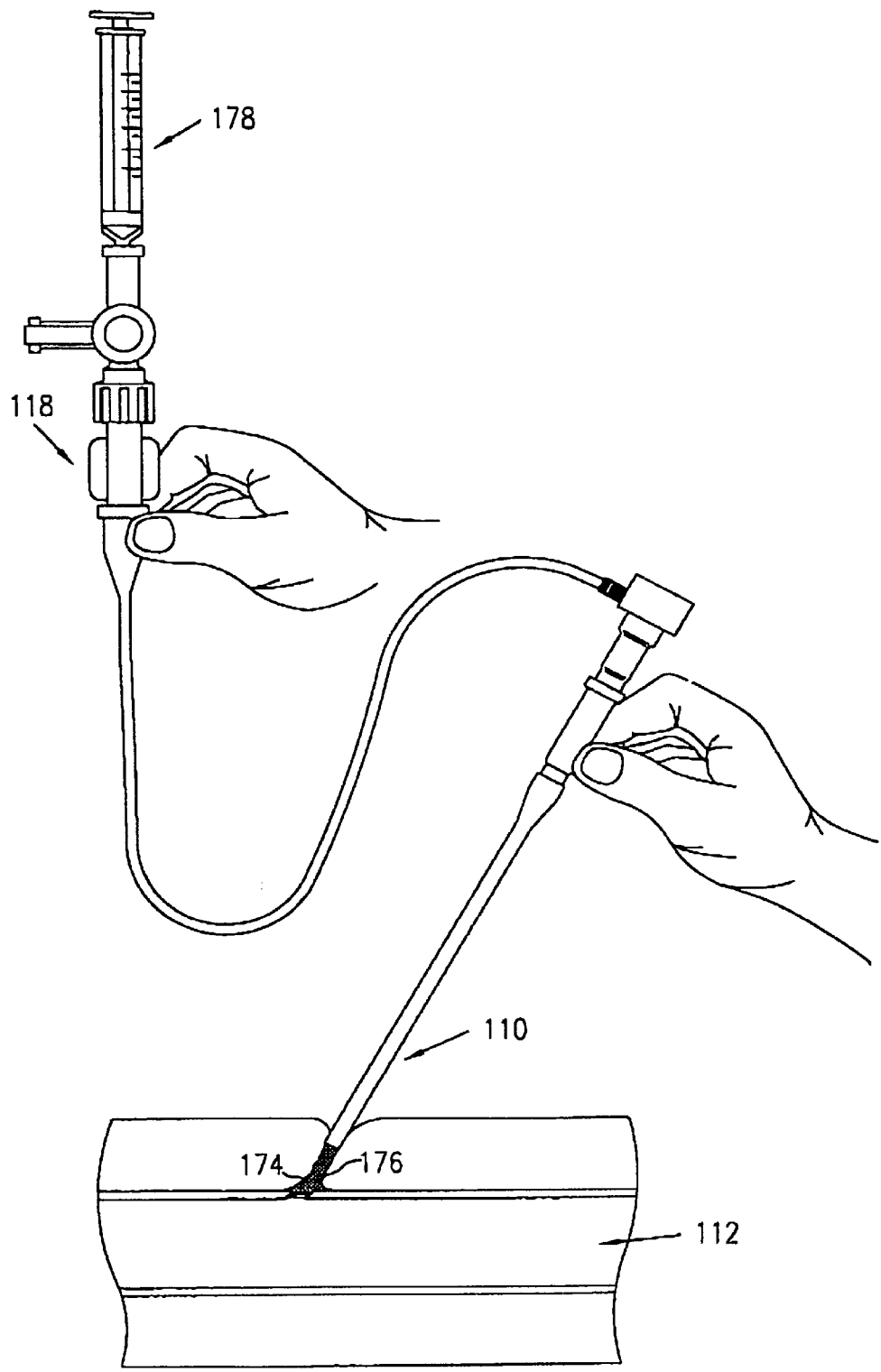
FIG. 22 is an illustration of injection of a hemostatic agent following the step illustrated in FIG. 21.

Optionally, as illustrated in FIG. 22, a hemostatic agent 176 may be injected via the catheter introducer 110 to a location adjacent aperture 174 but outside the artery 112. This injection may employ a syringe 178 which may be coupled via pressure gauge 118.

It will be appreciated by persons skilled in the art that the present invention is not limited by what has been particularly shown and described hereinabove. Rather the scope of the present invention includes both combinations and subcombinations of the various features described hereinabove and shown in the drawings as well as modifications and further developments thereof which would occur to a person of ordinary skill in the art upon reading the foregoing description and which are not in the prior art.

What is claimed is:

1. A method for hemostasis of an artery having a puncture after arterial catheterization, said catheterization using an introducer sheath, the method comprising the steps of:

inserting into an artery a catheter introducer having a forward end and a balloon adjacent said forward end prior to arterial catheterization;

following arterial catheterization and removal of a catheter from the catheter introducer, introducing an inflatable anchor into the artery via the catheter introducer;

inflating the inflatable anchor inside the artery;

retraction of the anchor, until it engages the forward end of said catheter introducer and further engages an inner wall surface of a wall of the artery, whereby the catheter introducer is also retracted such that the forward end thereof lies in the vicinity of the wall of the artery, whereby the anchor blocks blood flow from the artery at the catheter introducer and the balloon adjacent the forward end of the catheter introducer lies outside an outer surface of the wall of the artery;

inflating the balloon adjacent the forward end of the catheter introducer sufficiently to cause the forward end of the catheter introducer to be withdrawn completely from the wall of the artery and simultaneously to prevent blood flow from the artery through the artery wall;

deflating the inflatable anchor and withdrawal thereof from the artery; and following hemostasis, deflating of the balloon adjacent the forward end of the catheter introducer and removal of the catheter introducer from the patient.

2. A method according to claim 1 and also comprising injecting a hemostatic agent via the catheter introducer to a location external of the artery.

3. Apparatus for hemostasis of an artery having a puncture after arterial catheterization, the apparatus comprising a catheter introducer having a forward end and a balloon adjacent said forward end, wherein the catheter introducer is constructed such that inflation of the balloon adjacent the forward end of the catheter introducer in engagement with an outer wall surface of the artery causes the forward end of the catheter introducer to be withdrawn completely from the wall of the artery and spaced therefrom.

4. Apparatus according to claim 3 and also comprising an inflatable anchor suitable for introduction into an artery via the catheter introducer.

5. Apparatus according to claim 4 and also comprising an injector for injecting a hemostatic agent via the catheter introducer to a location external of the artery.

6. Apparatus according to claim 4 and also comprising a selectable inflator for inflating the inflatable anchor inside the artery.

7. Apparatus according to claim 6 and also comprising an injector for injecting a hemostatic agent via the catheter introducer to a location external of the artery.

8. Apparatus for hemostasis according to claim 6 and wherein the forward edge of the catheter introducer extends forwardly less than the extent of the balloon when inflated.

9. Apparatus for hemostasis according to claim 8 and wherein the forward edge of the catheter introducer extends less than 4 mm beyond the forward edge of the balloon when not inflated.

10. Apparatus for hemostasis according to claim 6 and wherein the forward edge of the catheter introducer extends less than 4 mm beyond the forward edge of the balloon when not inflated.

11. Apparatus according to claim 3 and also comprising a selectable inflator for inflating the inflatable anchor inside the artery.

12. Apparatus for hemostasis according to claim 11 and wherein the forward edge of the catheter introducer extends forwardly less than the extent of the balloon when inflated.

13. Apparatus for hemostasis according to claim 12 and wherein the forward edge of the catheter introducer extends less than 4 mm beyond the forward edge of the balloon when not inflated.

14. Apparatus for hemostasis according to claim 11 and wherein the forward edge of the catheter introducer extends less than 4 mm beyond the forward edge of the balloon when not inflated.

15. Apparatus for hemostasis according to claim 4 and wherein the forward edge of the catheter introducer extends forwardly less than the extent of the balloon when inflated.

16. Apparatus for hemostasis according to claim 15 and wherein the forward edge of the catheter introducer extends less than 4 mm beyond the forward edge of the balloon when not inflated.

17. Apparatus for hemostasis according to claim 4 and wherein the forward edge of the catheter introducer extends less than 4 mm beyond the forward edge of the balloon when not inflated.

18. Apparatus according to claim 3 and also comprising an injector for injecting a hemostatic agent via the catheter introducer to a location external of the artery.

19. Apparatus for hemostasis according to claim 18 and wherein the forward edge of the catheter introducer extends forwardly less than the extent of the balloon when inflated.

20. Apparatus for hemostasis according to claim 18 and wherein the forward edge of the catheter introducer extends less than 4 mm beyond the forward edge of the balloon when not inflated.

21. Apparatus for hemostasis according to claim 19 and wherein the forward edge of the catheter introducer extends less than 4 mm beyond the forward edge of the balloon when not inflated.

22. Apparatus according to claim 3 and also comprising an anchor suitable for introduction into an artery via the catheter introducer.

23. Apparatus for hemostasis according to claim 3 and wherein the forward edge of the catheter introducer extends forwardly less than the extent of the balloon when inflated.

24. Apparatus for hemostasis according to claim 23 and wherein the forward edge of the catheter introducer extends less than 4 mm beyond the forward edge of the balloon when not inflated.

25. Apparatus for hemostasis according to claim 3 and wherein the forward edge of the catheter introducer extends less than 4 mm beyond the forward edge of the balloon when not inflated.

26. A method for hemostasis of an artery having a puncture after arterial catheterization, said catheterization using an introducer sheath, the method comprising the steps of:

inserting into an artery a catheter introducer having a forward end prior to arterial catheterization;

following arterial catheterization, introducing a hemostasis catheter into the artery via the catheter introducer, said hemostasis catheter including an inflatable anchor at a forward end thereof and a balloon adjacent said forward end thereof and spaced from said inflatable anchor;

inflating the inflatable anchor inside the artery;

retraction of the hemostasis catheter, until the inflatable anchor engages the forward end of said catheter introducer and further engages an inner wall surface of a wall of the artery, whereby the anchor blocks blood flow from the artery and the balloon adjacent the forward end of the hemostasis catheter lies outside an outer surface of the wall of the artery;

removing the catheter introducer at least from the vicinity of the artery;

partially inflating the balloon adjacent the forward end of the hemostasis catheter sufficiently to prevent blood flow from the artery through the artery wall;

deflating of the inflatable anchor;

further inflating the balloon adjacent the forward end of the hemostasis catheter, sufficiently to cause the forward end of the hemostasis catheter to be withdrawn completely from the wall of the artery; and following hemostasis, deflating the balloon adjacent the forward end of the hemostasis catheter and removal of the hemostasis catheter from the patient.

27. A method according to claim 26 and also comprising injecting a hemostatic agent via the catheter introducer to a location external of the artery.

28. Apparatus for hemostasis of an artery having a puncture after arterial catheterization, the apparatus comprising:

an hemostasis catheter including an inflatable anchor at a forward end thereof and a balloon adjacent said forward end thereof and spaced from said inflatable anchor; and a selectable inflator for inflating the inflatable anchor inside the artery;

wherein the hemostasis catheter is constructed such that inflation of the balloon adjacent the forward end of the hemostasis catheter in engagement with an outer wall surface of the artery causes the forward end of the hemostasis catheter to be withdrawn completely from the wall of the artery and spaced therefrom.

29. Apparatus for hemostasis according to claim 28 and wherein the forward edge of the hemostasis catheter extends forwardly less than the extent of the balloon when inflated.

30. Apparatus for hemostasis according to claim 28 and wherein the forward edge of the hemostasis catheter extends less than 4 mm beyond the forward edge of the balloon when not inflated.

31. Apparatus for hemostasis according to claim 28 and wherein the forward edge of the hemostasis catheter extends less than 4 mm beyond the forward edge of the balloon when not inflated.

32. Apparatus for hemostasis of an artery having a puncture after arterial catheterization, the apparatus comprising:

an hemostasis catheter including an inflatable anchor at a forward end thereof and a balloon adjacent said forward end thereof and spaced from said inflatable anchor, said hemostasis catheter being constructed such that inflation of the balloon adjacent the forward end of the hemostasis catheter in engagement with an outer wall surface of the artery causes the forward end of the hemostasis catheter to be withdrawn completely from the wall of the artery and spaced therefrom.

33. Apparatus for hemostasis according to claim 32 and wherein the forward edge of the hemostasis catheter extends forwardly less than the extent of the balloon when inflated.

* * * * *